US012172962B2

(12) United States Patent
Zhao et al.

(10) Patent No.: US 12,172,962 B2
(45) Date of Patent: *Dec. 24, 2024

(54) DIAROYL CARBAZOLE COMPOUND AND USE THEREOF AS SENSITISING AGENT

(71) Applicant: IGM (ANQING) HIGH TECHNOLOGY DEVELOPMENT CO., LTD., Anhui (CN)

(72) Inventors: Wenchao Zhao, Nantong (CN); Jiaqi Li, Nantong (CN); Zhongli Ma, Nantong (CN); Chenlong Wang, Nantong (CN); Yonglin Wang, Nantong (CN)

(73) Assignee: IGM (ANQING) HIGH TECHNOLOGY DEVELOPMENT CO., LTD., Anhui (CN)

(*) Notice: Subject to any disclaimer, the term of this patent is extended or adjusted under 35 U.S.C. 154(b) by 452 days.

This patent is subject to a terminal disclaimer.

(21) Appl. No.: 17/598,936

(22) PCT Filed: Mar. 17, 2020

(86) PCT No.: PCT/CN2020/079714
§ 371 (c)(1),
(2) Date: Sep. 28, 2021

(87) PCT Pub. No.: WO2020/253283
PCT Pub. Date: Dec. 24, 2020

(65) Prior Publication Data
US 2022/0185775 A1 Jun. 16, 2022

(30) Foreign Application Priority Data

Jun. 21, 2019 (CN) .......................... 201910540381.5

(51) Int. Cl.
| *C07D 209/00* | (2006.01) |
| *C07D 209/86* | (2006.01) |
| *C08F 220/18* | (2006.01) |
| *C08F 222/02* | (2006.01) |
| *C09D 4/06* | (2006.01) |
| *C09D 7/61* | (2018.01) |
| *C09D 7/63* | (2018.01) |
| *C09D 11/037* | (2014.01) |
| *C09D 11/101* | (2014.01) |
| *C09D 11/107* | (2014.01) |
| *C09D 135/02* | (2006.01) |
| *C09J 4/06* | (2006.01) |
| *C09J 11/04* | (2006.01) |
| *C09J 11/06* | (2006.01) |
| *C09J 135/02* | (2006.01) |
| *G02B 5/20* | (2006.01) |
| *G03F 7/00* | (2006.01) |
| *G03F 7/029* | (2006.01) |

(52) U.S. Cl.
CPC .......... *C07D 209/86* (2013.01); *C07D 209/00* (2013.01); *C08F 220/1806* (2020.02); *C08F 222/02* (2013.01); *C09D 4/06* (2013.01); *C09D 7/61* (2018.01); *C09D 7/63* (2018.01); *C09D 11/037* (2013.01); *C09D 11/101* (2013.01); *C09D 11/107* (2013.01); *C09D 135/02* (2013.01); *C09J 4/06* (2013.01); *C09J 11/04* (2013.01); *C09J 11/06* (2013.01); *C09J 135/02* (2013.01); *G02B 5/20* (2013.01); *G03F 7/0007* (2013.01); *G03F 7/0295* (2013.01)

(58) Field of Classification Search
CPC ...... C07D 209/00; C07D 209/86; G02B 5/20; C08F 220/1806; C08F 222/02; C09D 4/06; C09D 7/61; C09D 7/63; C09D 11/037; C09D 11/107; C09D 11/101; C09D 135/02; C09J 4/06; C09J 11/04; C09J 11/06; C09J 135/02; G03F 7/0007; G03F 7/0295

See application file for complete search history.

(56) References Cited

U.S. PATENT DOCUMENTS

| 10,234,761 B2 | 3/2019 | Tanaka et al. |
| 2004/0170924 A1 | 9/2004 | Kunimoto et al. |
| 2009/0087759 A1 | 4/2009 | Matsumoto et al. |
| 2013/0188270 A1 | 7/2013 | Nishimae et al. |
| 2014/0220491 A1 | 8/2014 | Cho et al. |

(Continued)

FOREIGN PATENT DOCUMENTS

| CN | 1922142 A | 2/2007 |
| CN | 101321727 A | 12/2008 |
| CN | 100528838 C | 8/2009 |

(Continued)

OTHER PUBLICATIONS

Jian Huang, Zeng Xu, Zheyi Cai, Jingjing Guo, aJiali Guo, Pingchuan Shen, Zhiming Wang,Zujin Zhao, Dongge Ma, and Ben Z, Tang Robust luminescent small molecules with aggregation-induced delayed fluorescence for efficient solution-processed OLEDs, J. Mater. Chem. C, 2019, 7, 330-339 (Year: 2019).*

(Continued)

*Primary Examiner* — Bijan Ahvazi
(74) *Attorney, Agent, or Firm* — Irving M. Fishman

(57) ABSTRACT

Provided in the present invention is a novel diaroyl carbazole compound, used together with a carbazolyl oxime ester photoinitiator to show a significant synergistic initiation effect in a photoresist composition; the best sensitising effect is shown when the molar ratio of the diaroyl carbazole compound and the carbazolyl oxime ester photoinitiator is 0.1-1.4.

17 Claims, No Drawings

(56) References Cited

U.S. PATENT DOCUMENTS

| | | | |
|---|---|---|---|
| 2017/0283520 A1 | 10/2017 | Sawamoto et al. | |
| 2020/0004146 A1 | 1/2020 | Nishimae et al. | |

FOREIGN PATENT DOCUMENTS

| | | | |
|---|---|---|---|
| CN | 101508744 A | 8/2009 | |
| CN | 101528693 A | 9/2009 | |
| CN | 101528694 A | 9/2009 | |
| CN | 102924366 A | 2/2013 | |
| CN | 102924710 A | 2/2013 | |
| CN | 103153952 A | 6/2013 | |
| CN | 103492948 A | 1/2014 | |
| CN | 105358527 A | 2/2016 | |
| CN | 104284888 B | 10/2017 | |
| CN | 107678245 A | 2/2018 | |
| CN | 107793502 A | 3/2018 | |
| EP | 240745 A | 1/2012 | |
| EP | 2963014 A1 | 1/2016 | |
| JP | 2002241531 | 11/2002 | |
| JP | 2005343347 | 12/2005 | |
| JP | 2005343847 A | 12/2005 | |
| JP | 2007112930 A | 5/2007 | |
| JP | 2007219362 A * | 8/2007 | ............ C08F 2/50 |
| JP | 2009-519904 A | 5/2009 | |
| JP | 2013001713 A | 1/2013 | |
| JP | 2014-500852 A | 1/2014 | |
| JP | 2015-509074 A | 3/2015 | |
| JP | 2015-523324 A | 8/2015 | |
| JP | 2015-165297 A | 9/2015 | |
| WO | 0049080 A | 8/2000 | |
| WO | 2012045736 A1 | 4/2012 | |
| WO | 2013083505 A1 | 6/2013 | |

OTHER PUBLICATIONS

FeifeiWang, ZhipengWang, HonghuaWang and Guangyuan Zhou, Carbazole-based poly(aryl ether keton) containing crosslinkable allyl groups on the side chains: synthesis, characterization and properties, PolymInt 2015; 64: 858-866 (Year: 2015).*

Office Action from Counterpart Application JP2021-560178 and 3 page translation thereof.

2nd Office Action in Corresponding Korean Application KR 10-2021-7039140; Office Action dated Apr. 7, 2024; 4 pages.

English Translation of relevant portion of 2nd Office Action in corresponding Korean Application KR 10-21-21-7039140; 1 page.

International Search Report from PCT/CN2020/079714.

Written Opinion of the International Sesarch Authority in PCT/CN2020/079714.

Wang. Feifei et al. "Carbazole-based poly(aryletherketone) containing crosslinkable allyl groups on the side chains: synthesis. characterization and properties" Polymer International, vol. 64, No. 7, Jan. 13, 2015 (Jan. 13, 2015), ISSN: 0959-8103, pp. 858-866.

(Wang. Feifei et al.) (Properties of Poly (arylene ether ketone) s Containing N-Alkylcarbazole in Main Chains) Chinese Journal of Applied Chemistry, vol. 32, No. 4, Apr. 30, 2015 (Apr. 30, 2015), ISSN: 1000-0518, pp. 379-385.

Decision on Refusal in Japanese Patent Application JP2021-560178 corresponding to present application U.S. Appl. No. 17/598,936 (2 pages) and English translation thereof (2 pages).

First Office Action in Korean Patent Application KR10-2021-7039140 corresponding to present application U.S. Appl. No. 17/598,936 (13 pages) and English translation thereof (14 pages).

First Office Action in Chinese Patent Application CN20208001922.8 corresponding to present application U.S. Appl. No. 17/598,936 (8 pages) and English translation thereof (7 pages).

First Office Action in German Patent Application DE 11 2020 002 202.1 corresponding to present application U.S. Appl. No. 17/598,936 (10 pages) and English translation thereof (2 pages).

Wang, Feifei et al; Polymer Int 2015; 64:258-266; Synthesis and characterization of soluble poly(arylene ether ketone) s with high glass transition temperature based on 3,6-bi(4-fluorobenzoyl)-N-alkylcarbazole. (Published Online in Wiley Online Library Aug. 26, 2014).

Wang, Feifei, et al; Polymer Int 2015; 64:258-266; Carbazole-based poly(arylene ether ketone) containing crossslinkable allyl groups on the side chains: synthesis, characterization and properties (Published Online in Wiley Online Library Jan. 13, 2015).

Office Action from Counterpart Application JP2021-560178 filed Mar. 17, 2020; 5 pages. A 3 page English translation thereof has been previously submitted.

Taiwan Patent Application 109109042 (corresponding to U.S. Appl. No. 17/598,936), Office Action Jan. 25, 2022 (9 pages).

English Translation of Taiwan Patent Application 109109042 (corresponding to U.S. Appl. No. 17/598,936), Office Action Jan. 25, 2022 (5 pages).

Feifei Wang, et al; Carbazole-based poly(aryl ether ketone) containing crosslinkable allyl groups on the side chains: synthesis, characterization and properties; Polym Int 2015; 64:858-866 (9 pages).

Office Action dated Nov. 23, 2023 from Counterpart Application JP2021-560178 filed Mar. 17, 2020; 2 page English translation.

2nd Office Action, dated Jun. 15, 2024 of corresponding Chinese Patent Application CN202080012922.8 (5 pages) with English translation (6 pages).

* cited by examiner

DIAROYL CARBAZOLE COMPOUND AND USE THEREOF AS SENSITISING AGENT

TECHNICAL FIELD

The present invention belongs to the technical field of organic chemistry and photocuring technique, and particularly relates to a novel diaroyl carbazole compound, which is used as a high-activity sensitizing agent to form a photoinitiator composition together with a carbazolyl oxime ester, showing high sensitivity for use in a photocurable composition, especially in a photoresist.

BACKGROUND

Photocuring technique has been widely used since 1970s. For example, UV photocuring technique is widely used in the fields of coatings, printing inks and electronic device manufacturing. Photoinitiators and co-initiators such as sensitizing agents are key factors affecting curing efficiency. Carbazolyl oxime ester is an important class of oxime ester photoinitiators, and is well known, studied and used by those skilled in the art due to its relatively high sensitivity. For example, carbazolyl oxime ester compounds with various substituents and their use in materials or devices such as color filters, black matrixes, optical spacers and liquid crystal segmentation orientation were disclosed in CN1922142A (Mitsubishi Chemical), CN100528838C (02), CN101528694A (831), CN101528693A, CN101508744A (304), CN103153952A (03), CN103492948A and, CN107793502A. In order to improve the color saturation or hiding power, the content of pigment in the photocurable formula is getting higher and higher, especially in black photoresists, while the light energy utilization rate in the curing process is reduced due to the absorption by pigment. Therefore, it is necessary to develop a photoinitiator or a photoinitiator composition with higher sensitivity. Further, sensitizing the existing photoinitiators is also one of the methods to improve the sensitivity. Sensitizing agents described in the prior art such as CN100528838C includes benzophenone and derivatives thereof, thioxanthone and derivatives thereof, anthraquinone and derivatives thereof, coumarin derivatives, camphorquinone, phenothiazine and derivatives thereof, 3-(aroylmethylene) thiazolines, rhodanine and derivatives thereof, cosine, rhodamine, acridine, anthocyanin, merocyanine dyes and tertiary amine compounds, wherein benzophenone and derivatives thereof, thioxanthone and derivatives thereof, anthraquinone and derivatives thereof, and coumarin derivatives are preferred. Experiments show that these sensitizing agents do not show satisfactory sensitizing effect when mixing with carbazolyl oxime ester. Some compounds such as eosin, anthocyanin and phenothiazine even reduce the photocuring efficiency of photocurable composition formula due to the presence of phenolic hydroxyls or anilino groups. As for the four preferred kinds of compounds, although they are photoinitiators themselves, they have much lower photoinitiation efficiency than carbazolyl oxime ester compounds, and they do not show synergistic sensitizing effect when mixing with carbazolyl oxime ester. Therefore, there is actually no ideal sensitizing agent in the prior art.

However, there is an ever-growing need in the art to improve the performances such as exposure sensitivity, resolution, thermal stability, etc. The existing products and formula technologies are constantly facing new challenges.

SUMMARY OF THE INVENTION

A new class of new diaroyl carbazole compounds of formulas I and II are synthesized by the inventors of the present invention. It is surprisingly found that the new diaroyl carbazole compounds show a significant sensitising effect when they are used together with carbazolyl oxime ester, such as Trgacure®OXE 03, at a specific ratio, and their sensitising effects are significantly higher than that of those compounds disclosed in the prior art. Therefore, a photoinitiator composition comprising the above diaroyl carbazole compound and carbazolyl oxime ester is provided, and use of the photoinitiator composition in a photocurable composition, particularly in a photoresist is provided.

In a first aspect, provided is a diaroyl carbazole compound of formula I or II,

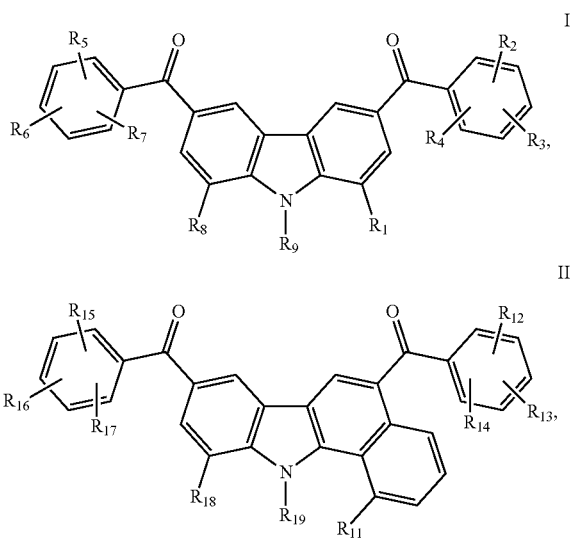

wherein, $R_1$, $R_8$, $R_{11}$ and $R_{18}$ are each independently selected from the group consisting of H, halogen, C1-C8 alkyl, C1-C8 O-alkyl and CN;

$R_2$, $R_3$, $R_4$, $R_5$, $R_6$, $R_7$, $R_{12}$, $R_{13}$, $R_{14}$, $R_{15}$, $R_{16}$ and $R_{17}$ are each independently selected from the group consisting of H, F, Cl, COOR$_{20}$, C1-C12 straight or branched alkyl, and C1-C12 straight or branched alkoxy, wherein, the C1-C12 straight or branched alkyl is unsubstituted or substituted by one or more groups selected from the group consisting of phenyl, C3-C6 cycloalkyl, C3-C6 heterocyclic groups, F, Cl, COOR$_{21}$, OR$_{21}$, SR$_{21}$, PO(OC$_n$H$_{2n+1}$)$_2$, and Si(C$_n$H$_{2n+1}$)$_3$, and wherein n is an integer from 1 to 4;

provided that at least one substituent on a benzene ring of each benzoyl group is a fluorine atom or a fluoroalkyl-containing group;

$R_9$ and $R_{19}$ are each independently selected from the group consisting of C1-C12 straight or branched alkyl, C2-C12 alkenyl, C3-C12 alkenyl alkyl group, with hydrogen atoms on the carbon atoms being unsubstituted or substituted by one or more groups selected from the group consisting of phenyl, C3-C6 cycloalkyl, C3-C6 heterocyclic group, halogen, COOR$_{20}$, OR$_{20}$, SR$_{20}$, PO(OC$_n$H$_{2n+1}$)$_2$ and Si(C$_n$H$_{2n+1}$)$_3$, wherein n is an integer from 1 to 4; or wherein the C3-C12 alkenyl alkyl is interrupted by one or more groups selected from the group consisting of O, S, SO, SO$_2$, CO, and COO;

or $R_9$ and $R_{19}$ are each independently C3-C12, with its alkyl chain being interrupted by one or more groups selected from the group consisting of O, S, SO, SO$_2$, and CO;

or R₉ and R₁₉ are each independently phenyl unsubstituted or substituted by one or more groups selected from the group consisting of C1-C8 alkyl, halogen, OR₂₀, SR₂₀, COR₂₀, CN, and COOH;

or R₉ and R₁, or R₉ and R₈ optionally form a C4-C6 heterocyclic structure;

or R₁₉ and R₁₁, or R₁₉ and R₁₈ optionally form a C4-C6 heterocyclic structure;

R₂₀ is C1-C12 alkyl or phenyl, unsubstituted or substituted by one or more groups selected from the groups consisting of phenyl, C3-C6 cycloalkyl, C3-C6 heterocyclic groups, F, Cl, OR₂₁, and SR₂₁; and R₂₁ is C1-C12 alkyl.

Preferably, the compound of formula I is selected from compounds of formula I-A and I-B; and the compound of formula II is selected from compounds of formula II-A and II-B:

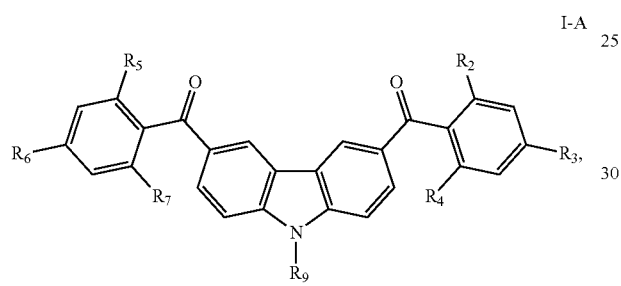

I-A

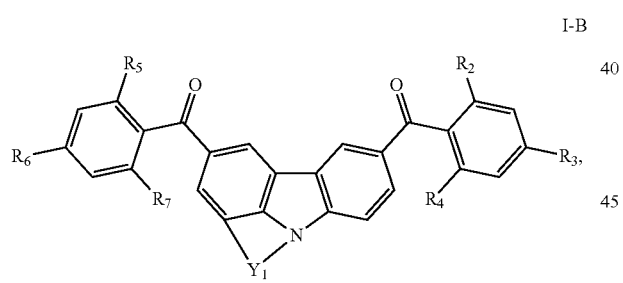

I-B

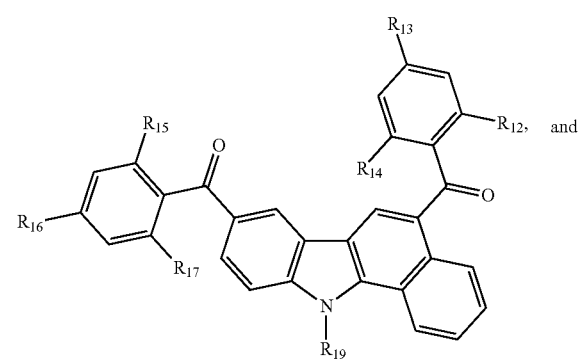

II-A

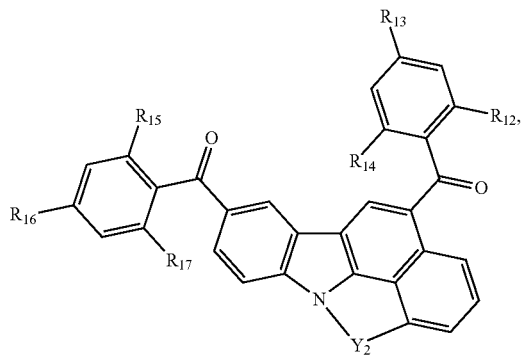

II-B wherein

R₂, R₃, R₄, R₅, R₆, R₇, R₁₂, R₁₃, R₁₄, R₁₅, R₁₆, and R₁₇ are each independently selected from the group consisting of H, F, Cl, COOR₂₀, C1-C12 straight or branched alkyl, C1-C12 straight or branched alkoxy, wherein the C1-C12 straight or branched alkyl is unsubstituted or substituted by one or more groups selected from the group consisting of phenyl, C3-C6 cycloalkyl, C3-C6 heterocyclic group, F, Cl, COOR₂₁, OR₂₁, SR₂₁, PO(OC$_n$H$_{2n+1}$)₂ and Si(C$_n$H$_{2n+1}$)₃, wherein n is an integer from 1 to 4;

provided that at least one substituent on the benzene ring of each benzoyl group is a fluorine atom or a fluoroalkyl-containing group;

R₉ and R₁₉ are as defined above; and

Y₁, Y₂ are each independently C2-C8 straight chain and branched alkyl groups, and the chain can be inserted by O, S, NR₂₁ or carbonyl, or hydrogen on the carbon may be substituted by OH or halogen atoms.

Preferably, diaroyl carbazole compounds of formula I-A and I-B are selected from the group consisting of following compounds:

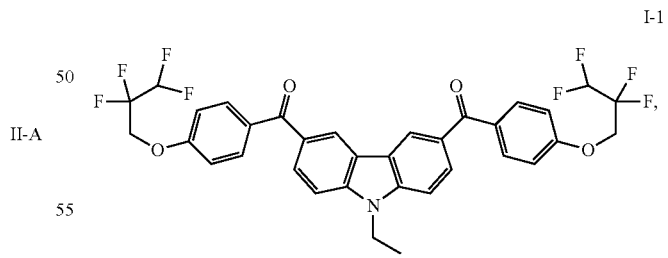

I-1

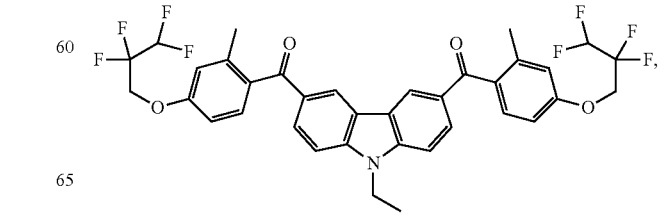

I-2

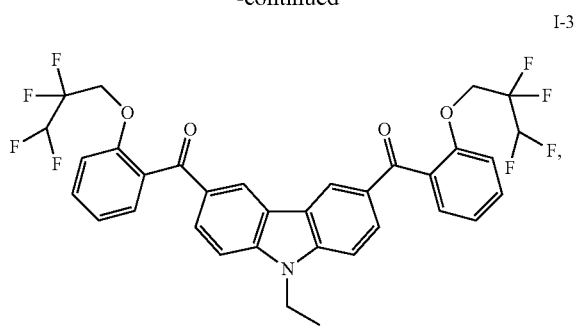

I-3

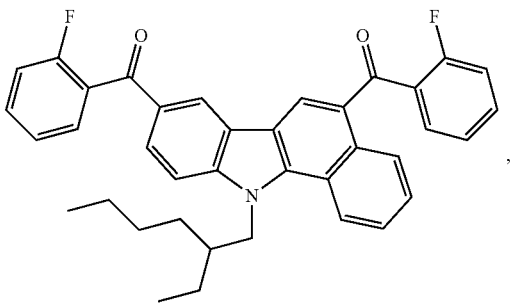

II-1

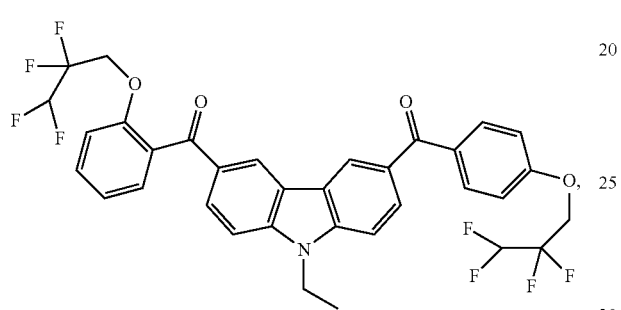

I-4

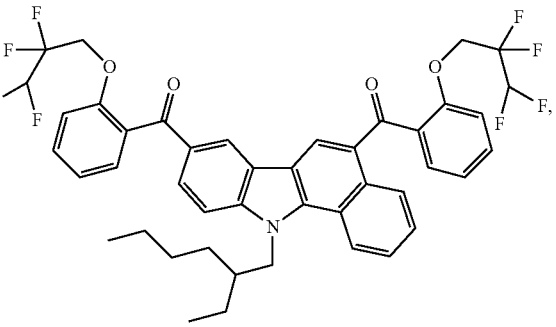

II-2

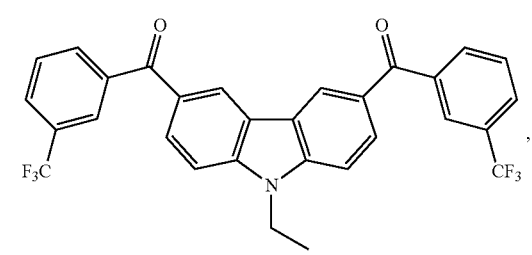

I-5

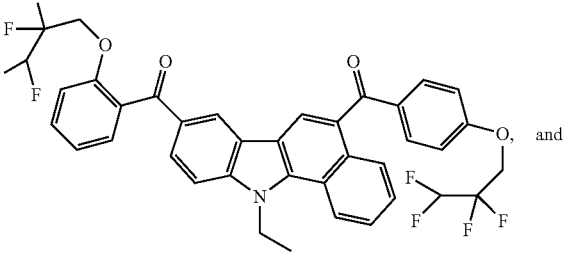

II-3

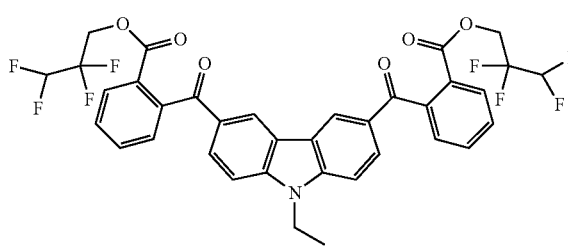

I-6

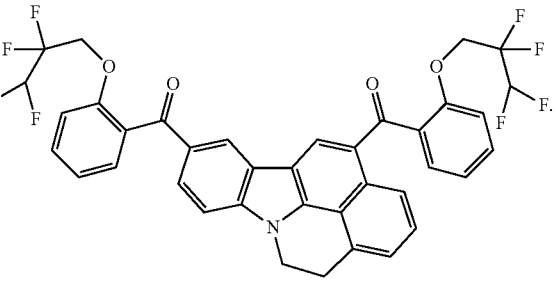

II-4

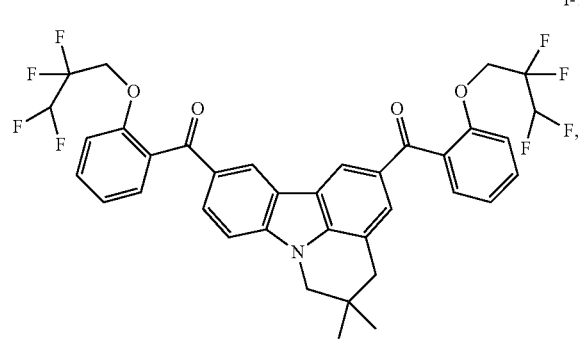

I-7

In a second aspect, provided is a method for preparing the diaroyl carbazole compound of formula I or II, comprising preparing a symmetric or asymmetric diaroyl compound via one-step or two-step Friedel-Crafts acylation reaction using a compound of formula III-A or formula III-B as a raw material reacting with a corresponding acylation reagent such as substituted aroyl chloride or acid anhydride; and optionally further carrying out aa esterification reaction or etherification reaction with an $R_{20}OH$ alcohol compound when any aryl group contains a carboxyl group or contains a halogen atom which is replaceable, obtaining a diaroyl carbazole compound of formula I or formula II:

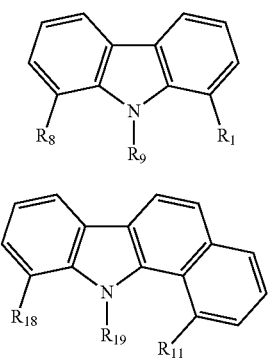

wherein $R_1$, $R_8$, $R_9$, $R_{11}$, $R_{18}$ and $R_{19}$ are as defined above.

In a third aspect, provided is a photoinitiator composition, comprising at least one of the above diaroyl carbazole compounds and at least one carbazolyl oxime ester photoinitiator, wherein the carbazolyl oxime ester photoinitiator comprises at least one oxime ester group

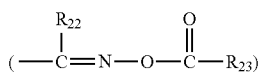

which is connected to a N-substituted carbazole parent structure directly or via a carbonyl group;

wherein, $R_{22}$ is C1-C12 alkyl unsubstituted or substituted with one or more groups selected from the group consisting of halogen, $OR_{24}$, $SR_{24}$, C3-C8 cycloalkyl, phenyl, C4-C20 heteroaryl, and $COOR_{24}$; or $R_{22}$ is C6-C20 aryl or C4-C20 heteroaryl, each unsubstituted or substituted by one or more groups selected from the group consisting of halogen, C1-C20 alkyl, one or more F-substituted C1-C8 alkyl, CN, $OR_{24}$, $SR_{24}$, and $NR_{25}R_{26}$; or $R_{22}$ is C6-C20 aroyl, C4-C20 heteroaryl;

$R_{23}$ is selected from the group consisting of C1-C12 alkyl, C6-C20 aryl, and C1-C4 alkoxy;

$R_{24}$ is selected from the group consisting of H, C1-C8 alkyl, phenyl, and C1-C20 alkyl phenyl, wherein the C1-C8 alkyl is optionally substituted by one or more of C3-C8 heterocyclic group, F and acetoxy;

$R_{25}$ and $R_{26}$ are each independently C1-C4 alkyl, or $OR_{24}$ substituted C2-C4 alkyl, or $NR_{25}R_{26}$ is a cyclic structure selected from

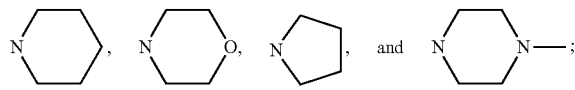

the carbazole parent structure is selected from the group consisting of carbazole, benzocarbazole and dibenzocarbazole, wherein hydrogen atoms on the parent structure are optionally substituted by one or more groups selected from C1-C20 alkyl, halogen, $NO_2$, CN, $OR_{27}$, C6-C20 aroyl, C4-C20 heteroaryl and 4,5-diphenylimidazole-2-yl in addition to the above oxime ester group or carbonyl group connected with the oxime ester group, and adjacent substituents on the parent structure optionally form a new five-membered to seven-membered ring structure; wherein C1-C20 alkyl is unsubstituted or substituted by one or more groups selected from halogen: halogen, C3-C8 cycloalkyl, C3-C8 heterocyclic group, phenyl, $COOR_{27}$, $OR_{27}$, $PO(OC_nH_{2n+1})_2$, and $Si(C_nH_{2n+1})_3$, wherein n is an integer from 1 to 4, or C1-C20 alkyl is interrupted by one or more oxygen atoms when the number of carbon atoms is greater than 3; $R_{27}$ is C1-C8 alkyl, or C3-C8 heterocyclic alkyl substituted C1-C8 alkyl; wherein aryl or heteroaryl in heteroaroyl in the C6-C20 aroyl and the C4-C20 heteroaroyl is unsubstituted or substituted by one or more groups selected from halogen, CN,

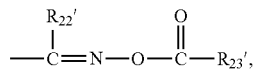

$R_{24}'$, $OR_{24}'$, $SR_{24}'$, $NR_{25}'R_{26}'$, $COOR_{24}'$, $R_{24}'SO_2$; $R_{22}'$, $R_{23}'$, $R_{24}'$, $NR_{25}'$, $R_{26}'$ have the same definition as corresponding $R_{22}$, $R_{23}$, $R_{24}$ and $NR_{25}R_{26}$.

Preferably, the carbazolyl oxime ester photoinitiator is selected from the group consisting of the following compounds and any combination thereof:

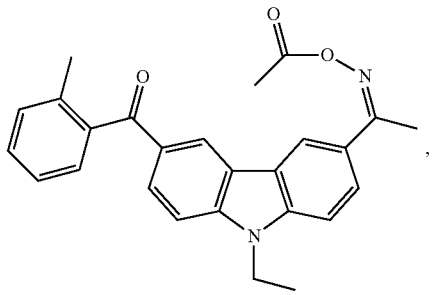

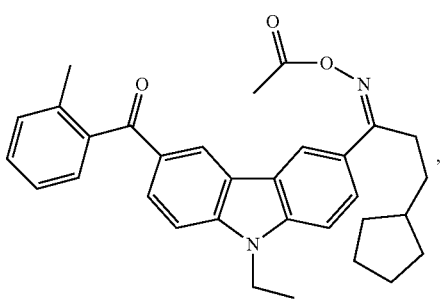

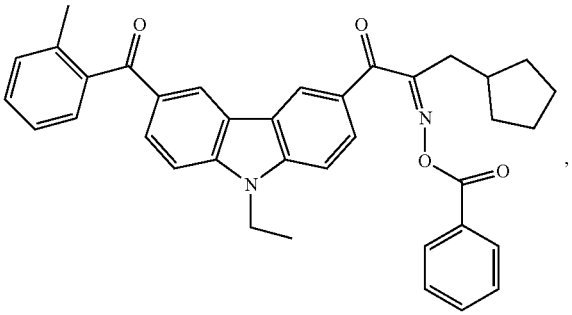

-continued
IV-4
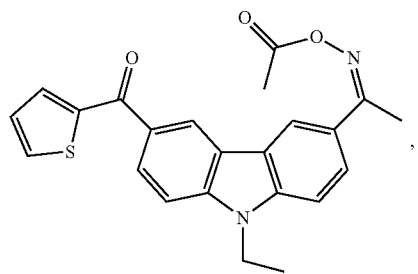
IV-5
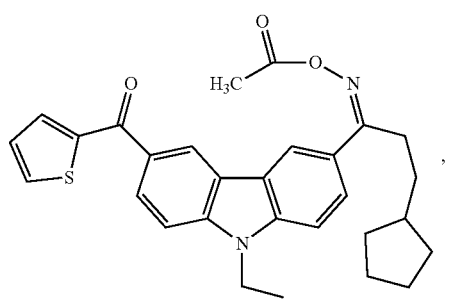
IV-6
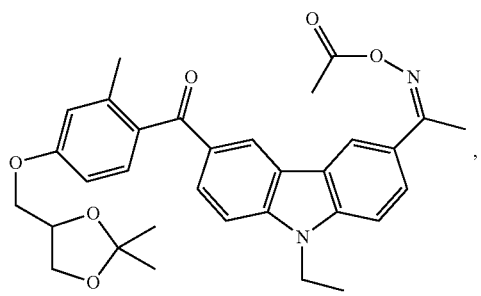
IV-7
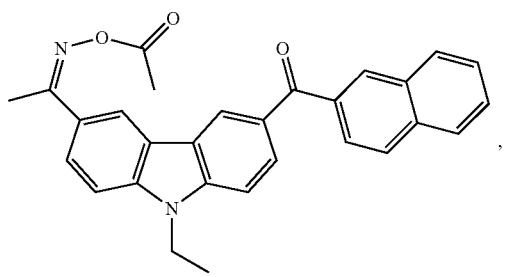
IV-8
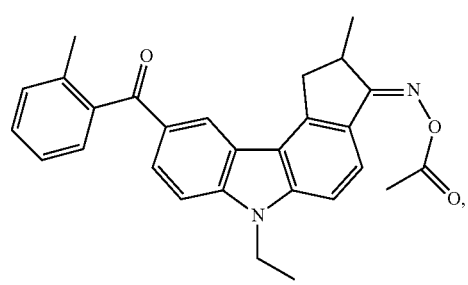
-continued
IV-9
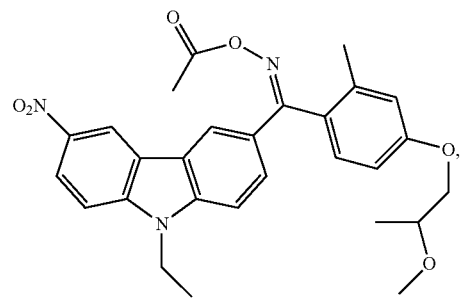
IV-10
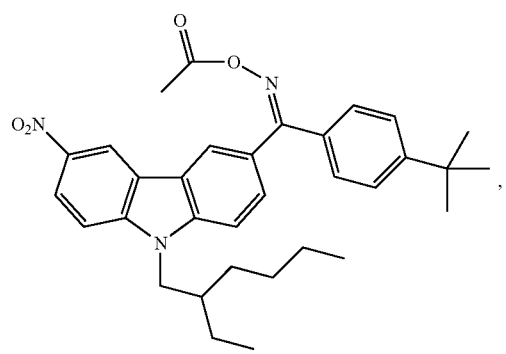
IV-11
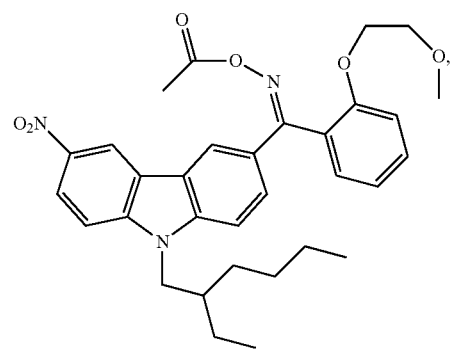
IV-12
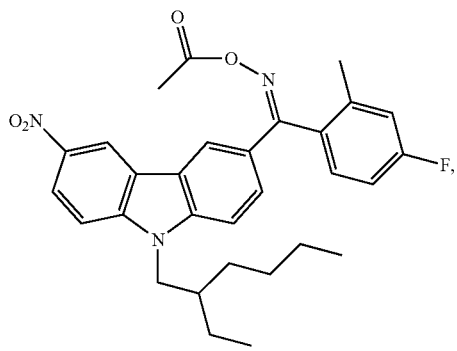

IV-13
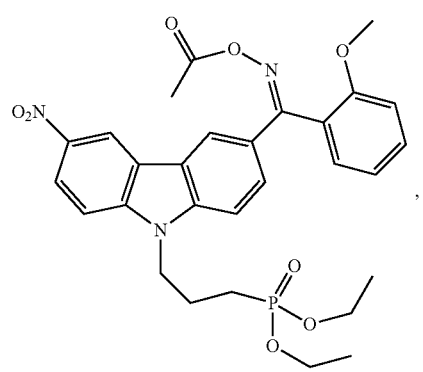
IV-14
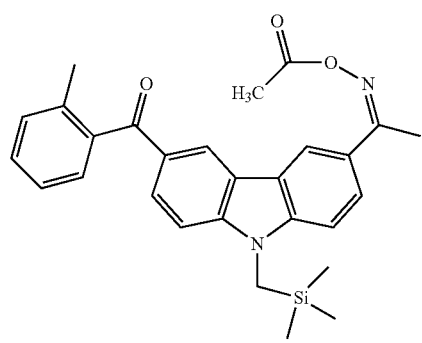
IV-15
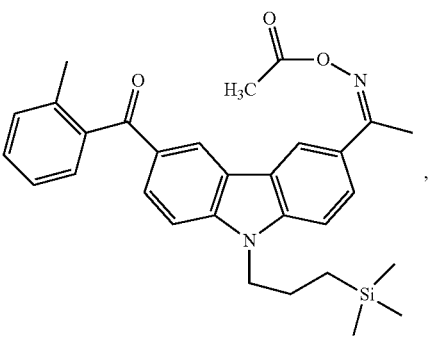
IV-16
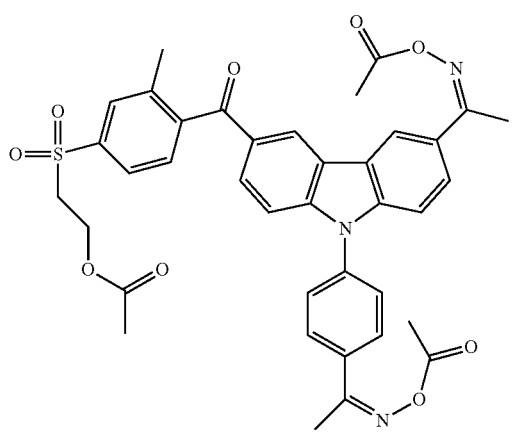
IV-17
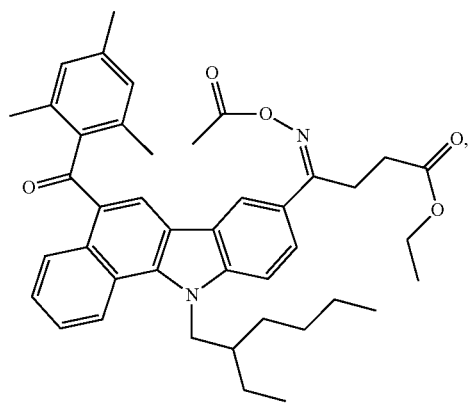
IV-18
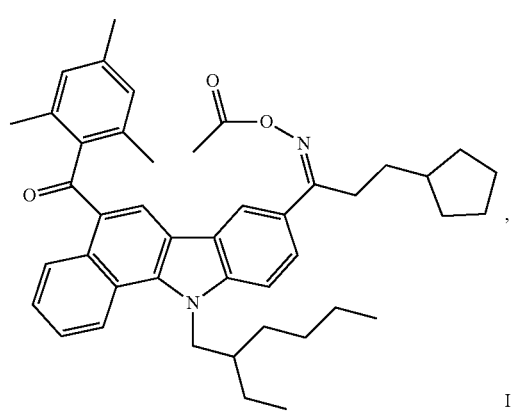
IV-19
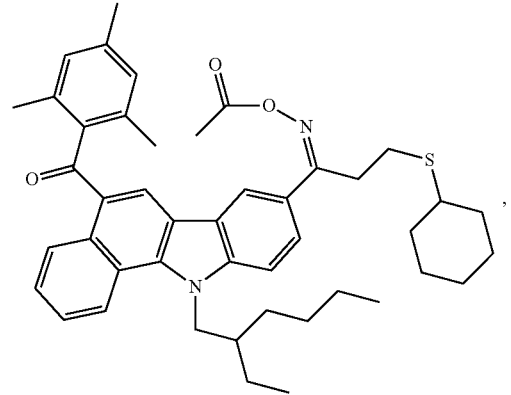
IV-20
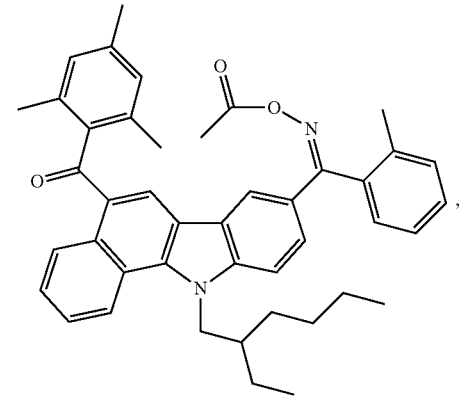

IV-21
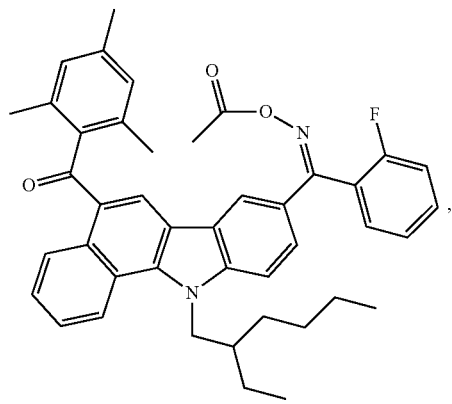
IV-22
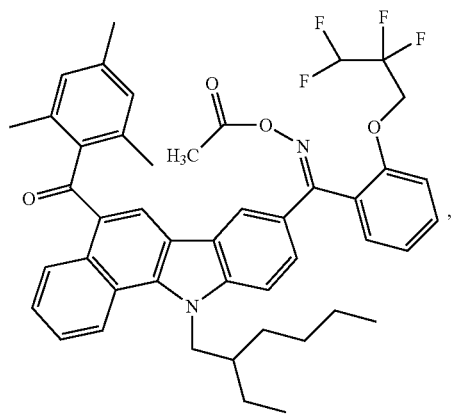
IV-23
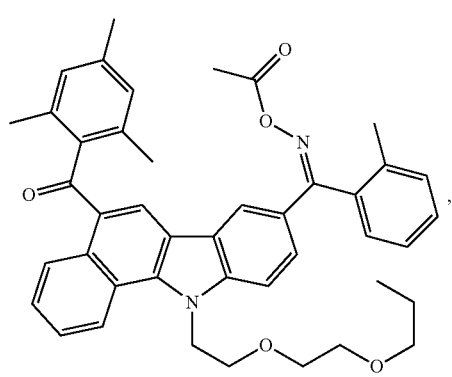
IV-24
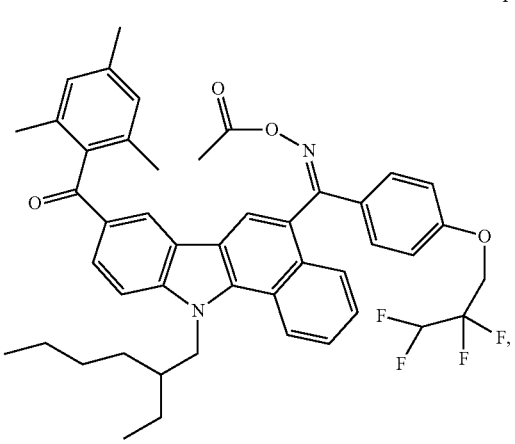
IV-25
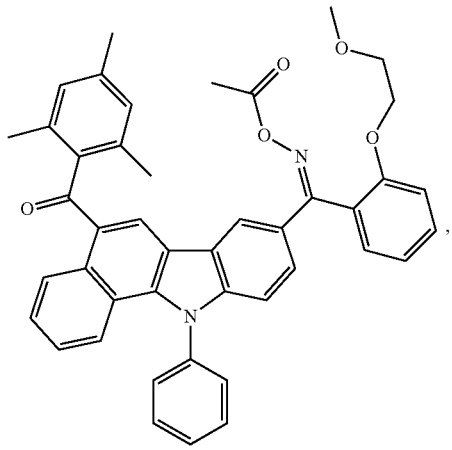
IV-26
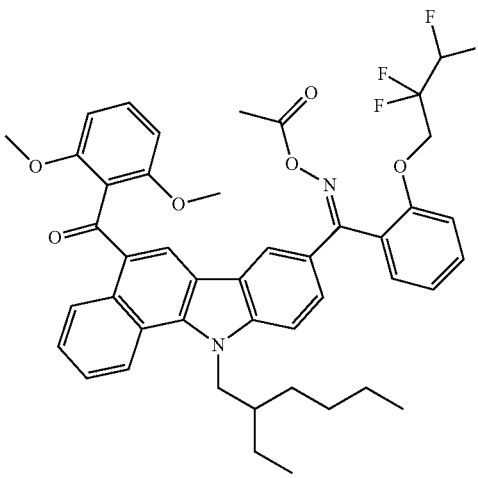
IV-27
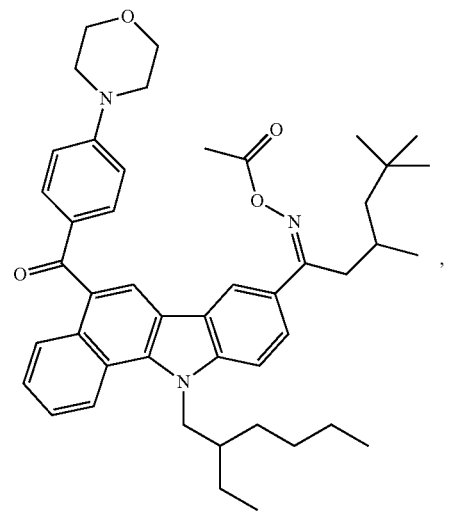

-continued
IV-28
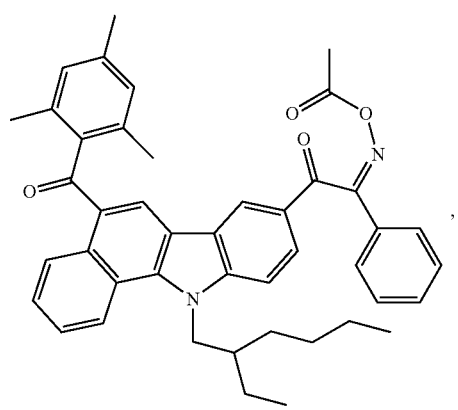
IV-29
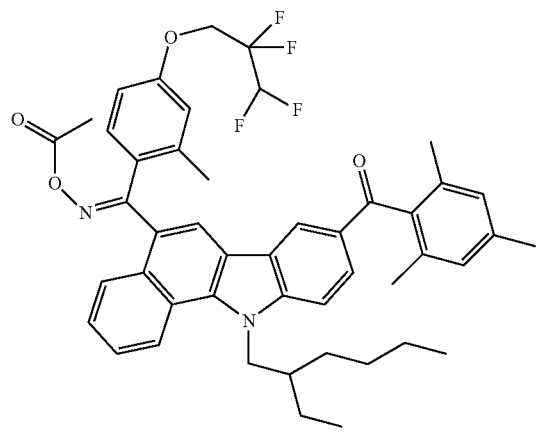
IV-30
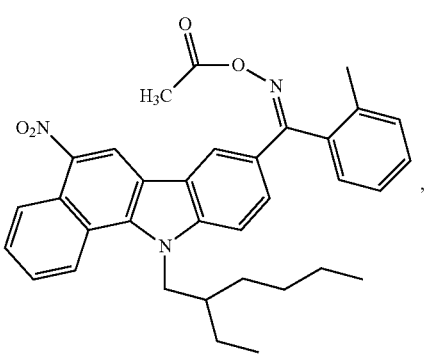
IV-31
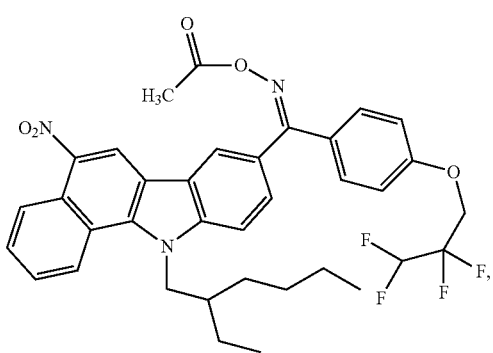
IV-32
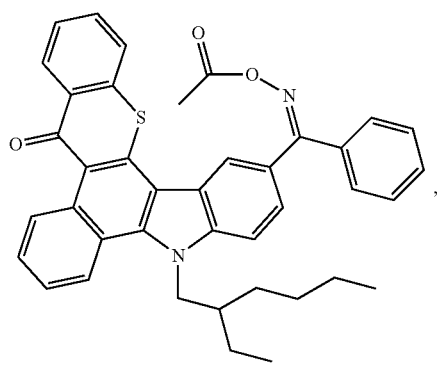
IV-33
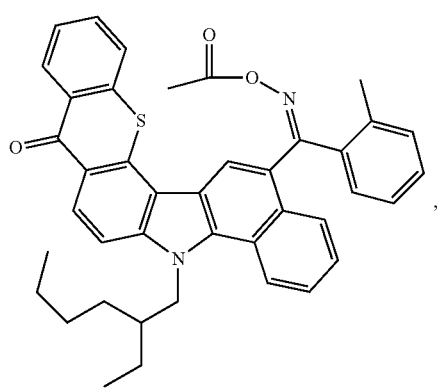
IV-34
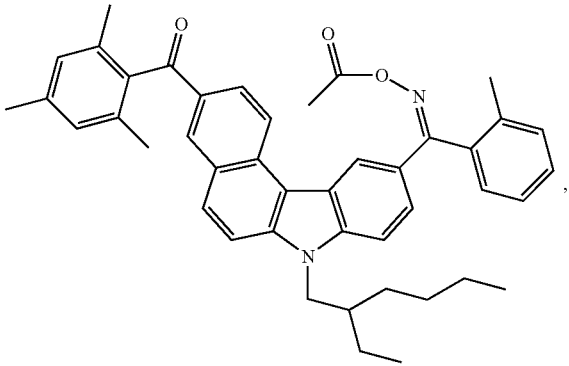
IV-35
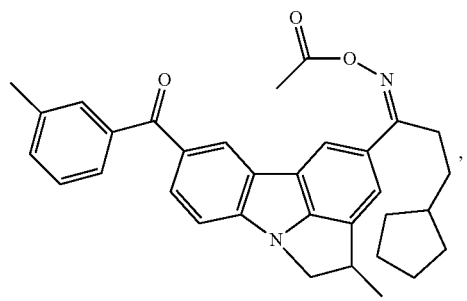

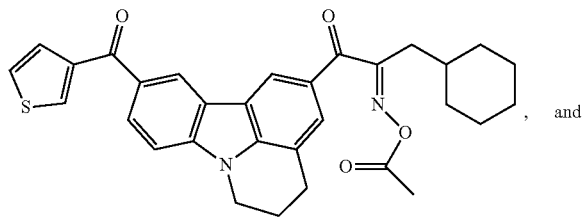

IV-36

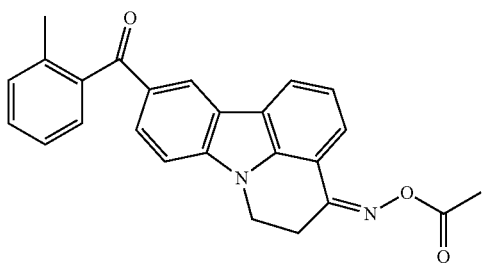

IV-37

The carbazolyl oxime ester can be prepared for example via oximation and esterification using corresponding acyl-carbazole parent compounds as a raw material. There are many related methods in prior art for preparing the carbazolyl oxime ester, such as the methods disclosed in CN103153952A.

A preferred method for preparing the photoinitiator composition comprises: well mixing 0.1 mol of a sensitizing agent compound such as a compound of formula I-1 with 0.1 mol of a carbazolyl oxime ester such as a compound of formula IV-22 to obtain a photoinitiator composition. Alternatively, the photoinitiator composition can be prepared by directly mixing one or more sensitizing agent compounds with one or more carbazolyl oxime esters and other components, wherein a ratio of a total molar amount of the sensitizing agent to a total molar amount of the carbazolyl oxime ester is not greater than 2:1, preferably is 0.1:1 to 1.4:1, and more preferably is 0.22:1 to 1.16:1.

In a fourth aspect, the present invention further provides a photocurable composition, comprising:
- a. a photoinitiator composition, comprising at least one sensitizing agent of formula I, II-A or II-B and at least one carbazole oxime ester compound of any one of formulas IV1 to IV37; optionally, component a accounts for 1-10%, preferably 1-8% by weight of a total weight of all solids in the formulation; and
- b. at least one radically polymerizable compound; optionally, the radically polymerizable compound is selected from the group consisting of an acrylate compound, a methacrylate compound, a resin containing acrylate or methacrylate groups, and any combination thereof.

As for the radically polymerizable compounds, examples of compounds having a low molecular weight include alkyl acrylate, cycloalkyl acrylate, hydroxyalkyl acrylate, dialkylaminoalkyl acrylate, alkyl methacrylate, cycloalkyl methacrylate, hydroxyalkyl methacrylate, and dialkylaminoalkyl methacrylate, such as methyl acrylate, butyl acrylate, cyclohexyl acrylate, 2-hydroxyethyl acrylate, isobornyl acrylate, ethyl methacrylate, and polysiloxane acrylate; other examples include acrylonitrile, vinyl acetate, vinyl ether, styrene, and N-vinyl-2-pyrrolidone. Examples of compounds containing two or more double bonds include ethylene glycol, polyethylene glycol, propylene glycol, neopentyl glycol, diacrylate of 1,6-hexanediol, trihydroxymethane triacrylate, pentaerythritol tetraacrylate, dipentaerythritol hexaacrylate, vinyl acrylate, triallyl isocyanurate, etc. Examples of double bond compounds having a higher molecular weight include a large class of substances commonly known as oligomers generally having a molecular weight of 500-3000, such as acrylated epoxy resin, acrylated polyester resin unsaturated polyester resin, acrylated polyether resin, and acrylated polyurethane resin.

In a fifth aspect, the present invention also provides an ink or a coating, which comprises the above-mentioned photocurable composition, into which other necessary components can also be added depending on the required performance such as ink color, printing application, etc. The ink or coating can be used for pattern printing, 3D printing, PCB solder mask, liquid or dry film corrosion resistant materials, substrate protective coating, etc.

In a sixth aspect, the present invention also provides an adhesive, which comprises the above-mentioned photocurable composition, into which other necessary components can also be added depending on the required performance for the adhesive. The adhesive can be used for adhering glass, plastic, metal members, etc.

In addition to the materials listed herein, it is easy for those skilled in the art to add other necessary ingredients, such as stabilizers, surfactants, leveling agents and dispersants, according to the existing technology and use of the photocurable composition.

In a seventh aspect, the present invention also provides a photoresist, comprising:
- a. at least one of the above photoinitiator composition, optionally, the mass of which accounts for 0.2% to 10%, preferably 1% to 8% by weight of a total weight of all solids in the formulation,
- b. at least one radically polymerizable confound, such as a multifunctional acrylate monomer,
- c. an alkali soluble resin,
- d. a pigment, and
- e. a solvent.

Examples of the multifunctional acrylate monomer in component b include: dipentaerythritol hexaacrylate and pentaerythritol tetraacrylate. Examples of the alkali soluble resin in component c include copolymers obtained by copolymerizing of polyacrylate having a carboxylic acid group, such as methacrylic acid, itaconic acid, maleic acid, etc., and a common monomer such as methyl acrylate, butyl acrylate, benzyl acrylate, hydroxyethyl acrylate, styrene, butadiene, maleic anhydride, etc. Preferred examples of the copolymer include a copolymer of methyl methacrylate and methacrylic acid, a copolymer of benzyl methacrylate and methacrylic acid, a copolymer of methyl methacrylate, butyl methacrylate, methacrylic acid and styrene.

Examples of the pigment in component d include: C.I. pigment red 177, C.I. pigment green 7, C.I. pigment blue 15:6, solvent blue 25, carbon black, titanium black, and C.I. pigment black 1.

Component b, component c, component d and component e are described in many existing literatures such as CN103153952A, and those skilled in the art can make selections according to their needs.

In addition to the component a as a photoinitiator, other existing or commercial available photoinitiators or co-initiators, such as Omnirad BDK, Omnirad 369, Omnirad 379, Omnirad 389, Omnirad TPO, Omnirad 819, Omnirad ITX, Omnirad DETX, and Omnirad 784, can also be added, as long as it is beneficial to the performance of the photocurable composition, especially the photoresist, wherein, Omnirad is a commodity of IGM resin company.

In addition to the above components, other resins such as polyalkyl methacrylate, ethyl cellulose, carboxymethyl cellulose, linear phenolic resin, polyvinyl butyral, polyvinyl acetate, polyester and polyimide can be added.

In an eighth aspect, the present invention also provides a black photoresist. When the pigment in the photoresist is a well-dispersed black pigment such as carbon black or titanium black, it becomes a black photoresist. Black photoresist can be used to prepare a black matrix, a spacer of cell gap, and a microlens.

In a ninth aspect, a color filter device can be prepared by a color filter processing process using the photoresist and/or black photoresist of the present invention as raw materials, which is an important component of a color display screen.

Further provided is any article such as a color filer and a color display screen prepared by necessary processes using any materials comprising the photoinitiator composition of tire present invention such as an ink, a coating, an adhesive, a photoresist, and a black photoresist.

DETAILED DESCRIPTION OF THE EMBODIMENTS

The following embodiments and comparative examples are provided for illustrating the present invention in details.
Light Source Apparatus:
  365 nm LED surface light source, Lantian Special Light Development Co., Ltd.
Test Equipment:
  Stereo microscope, COVS-50G, Guangzhou Mingmei Optoelectronic Technology Co., Ltd., wherein the unit of line width is μm.
Experimental Materials:
  A compound of formula I-1, from compound preparation example 1;
  A compound of formula II-2, from compound preparation example 2;
  Omnirad DETX, a photoinitiator product of IGM Resin Company;
  Esacure 364, a photoinitiator product of IGM Resin Company;
  Omnirad EMK, a photoinitiator product of IGM Resin Company;
  OXE 02: a compound of formula IV-1, a photoinitiator product of BASF Company;
  OXE 03: a compound of formula IV-22, a photoinitiator product of BASF Company;
  NCI 831: a compound of formula IV-9, a product of ADEKA Company, Japan;
  PBG 304: a compound of formula IV-2, a product of Changzhou Qiangli Electronic New Material Co., Ltd.;
  Photomer 6010: aliphatic urethane triacrylate, a product of IGM Resin Company;
  DPHA: dipentaerythritol penta/hexaacrylate, a product of Tianjin Tianjiao Chemical Co., Ltd.;
  HPMA: polymaleic acid, a product of Aladdin Industries, USA.

COMPOUND PREPARATION EXAMPLES

Preparation of Diaroyl Carbazole Compounds

Preparation Example 1: Preparation of 9-ethyl-3,6-bis[4-(2,2,3,3-tetrafluoroproxy)benzoyl]carbazole (a compound of formula I-1)

1a. Preparation of 9-ethyl-3,6-bis(4-fluorobenzoyl)carbazole 19.5 g of N-ethyl carbazole is dissolved in 250 ml of dichloroethane, and 34 g of aluminum trichloride is added to obtain a solution. The temperature is kept at 0~5° C., and 40 g of p-fluorobenzoyl chloride is added drop wise into the solution, then the temperature is kept at 0~5° C. to react for 15 h. The reaction solution is added into 100 ml of 10% HCl solution of 0° C. in batches, followed by stirring for 30 min. After standing for 30 min, a dichloroethane phase is separated and washed with 50 ml of 2% sodium hydroxide solution for 30 min. The dichloroethane solution is vacuum distilled to recover dichloroethane. The residue is crystallized by adding 80 ml of ethyl acetate to obtain 30.5 g of a product as a white powder having a content of 98.5% and a yield of 69.5%.

1b. Preparation of 9-ethyl-3,6-bis [4-(2,2,3,3-tetrafluoropropoxy)benzoyl] carbazole 30 g of 9-ethyl-3,6-bis(4-fluorobenzoyl) carbazole prepared in step 1a, 25 g of 2,2,3,3-tetrafluoropropanol and 8 g of sodiam hydroxide are dissolved in 200 ml of pyridine and reacted at 70° C. for 18 h. Vacuum distillation is carried out to evaporate pyridine and redundant 2,2,3,3-tetrafluoropropanol. 100 ml of water and 250 ml of dichloroethane are added to the residue and stirred for 1 h. Then an aqueous phase is separated. The dichloroethane solution is washed twice with 100 ml of water, and vacuum distilled to recover dichloroethane. 150 ml of ethyl acetate and 2 g of activated carbon are added to the residue, followed by refluxing under heating for 1 h and filtering to remove activated carbon to obtain a filtrate. The filtrate is vacuum distilled to remove about 100 ml of ethyl acetate, then cooled to crystallize, and filtered. The filter cake is dried to obtain 27.8 g of a product as a light yellow powder having a content of 98.5% and a yield of 61.4%.

The structure is confirmed by $^1$H-NMR spectrum (CDCl$_3$), δ[ppm]: 1.512 (t, 3H), 4.425-4.483 (m, 6H), 5.949-6.277 (m, 2H), 7.016-7.045 (m, 4H), 7.496-7.517 (d, 2H), 7.844-7.868 (d, 4H), 7.990-8.011 (d, 2H), 8.534 (s, 2H).

Preparation Example 2: Preparation of 11-(2-ethylhexyl)-5,8bis[4-(2,2,3,3-tetrafluoropropoxy)benzoyl]-11H-benzo[z]carbazole (a compound of formula II-2)

2a. Preparation of 11-(2-ethylhexyl)-5,8-bis(4-fluorobenzoyl)-11H-benzo[a]carbazole 2.0 g of B03D is added into to a 50 ml single-necked flask, and 20 ml of dichloroethane is added to dissolve it, then 0.2 g of zinc chloride and 2.3 g of o-fluorobenzoyl chloride are added, and stirred and reacted at 80° C. for 10 h. After cooling, the reaction solution is washed twice with 20 ml of water, and then concentrated under reduced pressure to dryness to obtain 4.0 g of a brown viscous substance, which is used in the reaction of 2b without purification.

2b. Preparation of 11-(2-ethylhexyl)-5,8bis[4-(2,2,3,3-tetrafluoropropoxy)benzoyl]-11H-benzo[a]carbazole 4.0 g of 11-(2-ethylhexyl)-5,8-bis(4-fluorobenzoyl)-11H-benzo[a]carbazole obtained in step 2a is dissolved with 20 ml pyridine in a 50 ml single-necked flask, then 2.2 g of tetrafluoropropanol and 1.2 g of sodium hydroxide are added, heated to 80° C. and stirred for 5 h. The reaction solution is added dropwise to 100 ml of water, then stirred with 100 ml of dichloroethane for 1 h, and allowed to stand for separation. The separated dichloroethane solution is concentrated under reduced pressure to dryness to obtain 4.7 g of brown solid. The brown solid is dissolved under heating in a mixed solvent of 20 ml ethyl acetate and 20 ml ethanol, then 0.25 g activated carbon is added, followed by refluxing for 1 h. The resulted solution is hot filtered, and the filtrate is cooled down to precipitate a yellow crystal, which is dried to obtain 2.5 g product. The total yield of the two-step reaction is 51.3%, and the content of 11-(2-ethylhexyl)-5, 8bis[4-(2,2,3,3-tetrafluoropropoxy)benzoyl]-11H-benzo[a] carbazole is 98.51%.

The structure is confirmed by $^1$H-NMR spectrum (CDCl$_3$), δ[ppm]: 0.754-0.789 (m, 6H), 1.126-1.328 (m, 8H), 2.113 (s, 1H), 4.369-4.452 (t, 2H), 4.513-4.599 (t, 2H), 4.928 (m, 2H), 4.994-5.342 (m, 1H), 5.537-5.885 (m, 1H), 7.251-7.272 (m, 4H), 7.430-7.455 (d, 1H)), 7.566-7.811 (m, 6H), 7.950-7.979 (d, 1H), 8.430 (s, 1H), 8.571 (s, 1H), 8.668-8.695 (d, 1H). 8.736-8.764 (d, 1H)).

Preparation of Photoinitiator Compositions

Composition Preparation Example 1

12 g of the compound of formula II-2 and 28 g of OXE-02 are mixed and ground in a mortar to obtain 40 g of a composition. A molar ratio of the diaroyl carbazole compound to the carbazolyl oxime ester photoinitiator is 0.22.

Composition Preparation Example 2

12 g of the compound of formula I-1 and 28 g of OXE-02 are mixed and ground in a mortar to obtain 40 g of a composition. A molar ratio of the diaroyl carbazole compound to the carbazolyl oxime ester photoinitiator is 0.27.

Composition Preparation Example 3

12 g of the compound of formula I-1 and 12 g of OXE-03 are mixed and ground in a mortar to obtain 24 g of a composition. A molar ratio of the diaroyl carbazole compound to the carbazolyl oxime ester photoinitiator is 1.16.

Composition Preparation Example 4

12 g of the compound of formula II-2 and 28 g of OXE-03 28 g are mixed and ground in a mortar to obtain 40 g of a composition. A molar ratio of the diaroyl carbazole compound to the carbazolyl oxime ester photoinitiator is 0.41.
Preparation of Alkali-Soluble Resin 18 g of benzyl methacrylate, 6 g of methacrylic acid, 6 g of hydroxyethyl methacrylate, 1.5 g of azobisisobutyronitrile, 0.6 g of dodecanethiol, and 200 ml of toluene are added into a 1 L constant pressure dropping funnel, 100 ml of toluene is added into a 500 ml four-necked flask, air in the four-necked flask is replaced with nitrogen, and the temperature is increased to 80° C., then the solution in the funnel is added therein dropwise. After reacting for 6 h, the reaction solution is cooled down and filtered to obtain 24 g of a white alkali-soluble resin.

Photoresist Composition Examples and Comparative Examples

The examples and comparative examples are prepared according to the components described in tables 1 to 4.

The compositions prepared in the composition preparation examples can be used as the initiator and sensitizing agent, or can be mixed according to the proportion in the table and dissolved in the PMA, and then the composition solution is mixed with the black color paste in proportion. After the components are mixed well, the resulted is coated onto a glass slide using a 10 μm wire rod, and put into an oven for drying at 90° C. for 5 min. A 365 nm light source is used to perform curing with a 120 μm mask, and then development is carried out using a 1% NaOH solution at 25° C., followed by soaking and cleaning for 10 s with pure water. After diving in an oven at 90° C. for 30 minutes, the line width of the developed image is measured. The unit of line width is μm.

TABLE 1

|  | Examples | | | | Comarative examples | | | | |
| --- | --- | --- | --- | --- | --- | --- | --- | --- | --- |
|  | 1 | 2 | 3 | 4 | 1 | 2 | 3 | 4 | 5 |
| Compound of formula I-1 | 0.024 | 0.04 | 0.024 | 0.04 | 0 | 0.08 | 0.056 | 0.056 | 0 |
| OXE 02 | 0.056 | 0.04 | 0 | 0 | 0.08 | 0 | 0.024 | 0 | 0 |
| OXE 03 | 0 | 0 | 0.056 | 0.04 | 0 | 0 | 0 | 0.024 | 0.08 |
| PMA | 2 | 2 | 2 | 2 | 2 | 2 | 2 | 2 | 2 |
| black color paste | 4.5 | 4.5 | 4.5 | 4.5 | 4.5 | 4.5 | 4.5 | 4.5 | 4.5 |
| sensitizing agent/initiator molar ratio | 0.32 | 0.75 | 0.49 | 1.16 | 0 | 0 | 1.74 | 2.69 | 0 |

TABLE 2

|  | Example 5 | Example 6 | Comparative example 6 | Comparative example 7 |
| --- | --- | --- | --- | --- |
| Compound of formula I-1 | 0.024 | 0.024 | 0 | 0 |
| NCI 831 | 0.056 | 0 | 0.08 | 0 |
| PBG 304 | 0 | 0.056 | 0 | 0.08 |
| PMA | 2 | 2 | 2 | 2 |
| black color paste | 4.5 | 4.5 | 4.5 | 4.5 |
| sensitizing agent/initiator molar ratio | 0.27 | 0.23 | 0 | 0 |

TABLE 3

|  | Example 7 | Example 8 | Example 9 | Comparative examples | | | |
|---|---|---|---|---|---|---|---|
|  |  |  |  | 1 | 2 | 8 | 9 |
| Compound of formula II-2 | 0.024 | 0.04 | 0.024 | 0 | 0 | 0.056 | 0.08 |
| OXE 02 | 0 | 0 | 0.056 | 0.08 | 0 | 0 | 0 |
| OXE 03 | 0.056 | 0.04 | 0 | 0 | 0.08 | 0.024 | 0 |
| PMA | 2 | 2 | 2 | 2 | 2 | 2 | 2 |
| black color paste | 4.5 | 4.5 | 4.5 | 4.5 | 4.5 | 4.5 | 4.5 |
| sensitizing agent/initiator molar ratio | 0.41 | 0.96 | 0.27 | 0 | 0 | 2.24 | 0 |

TABLE 4

|  | Comparative 10 | Comparative 11 | Comparative 12 |
|---|---|---|---|
| Omnirad DETX | 0.024 | 0 | 0 |
| ESacure 3644 | 0 | 0.024 | 0 |
| Omnirad EMK | 0 | 0 | 0.024 |
| OXE 02 | 0.056 | 0.056 | 0.056 |
| PMA | 2 | 2 | 2 |
| black color paste | 4.5 | 4.5 | 4.5 |
| sensitizing agent/initiator molar ratio | 0.79 | 0.25 | 0.65 |

The examples and comparative examples in tables 1, 2 and 4 are used to perform coating, curing, developing, and measuring. The data are shown in tables 5, 6, 7 and 8. The results show that: examples where the compound of formula I-1 is used as a sensitizing agent in combination with various carbazolyl oxime esters at a ratio within the range of the present invention exhibit significantly better development effect than comparative examples in which a sensitizing agent is not used, or a sensitizing agent is used alone or the amount of sensitizing agent is outside the range of the present invention. In particular, the results of comparative example 2 show that the compound of formula I-1 alone cannot form a developed pattern, and has almost no effect of initiating polymerization. Comparing the formulations in table 4 and the data in table 8, it is found that the compound of formula I-1 as a sensitizing agent has significantly better sensitising effect than thioxanthone, coumarin and tetraethyl Michler's ketone, and the developing line width of the latter three is even smaller than that of comparative example 1 in which oxime ester is used alone.

The examples and comparative examples in table 3 are used to perform coating, curing, developing, and measuring. The data are shown in table 7. The results show that: examples where the compound of formula II-2 is used as a sensitizing agent in combination with various carbazolyl oxime esters at a ratio within the range of the present invention exhibit significantly better development effect than comparative examples in which a sensitizing agent is not used, or a sensitizing agent is used alone or the amount of sensitizing agent is outside the range of the present invention. In particular, the results of comparative example 9 show that the compound of formula II-2 alone cannot form a developed pattern, and has almost no effect of initiating polymerization. Comparing the formulations in table 4 and the data in table 8, it is found that the compound of formula II-2 as a sensitizing agent has significantly better sensitising effect than of thioxanthone, coumarin, and tetraethyl Michler's ketone.

TABLE 5

|  | Examples | | | | Comparative examples | | | | |
|---|---|---|---|---|---|---|---|---|---|
|  | 1 | 2 | 3 | 4 | 1 | 2 | 3 | 4 | 5 |
| Break point/s | 20 | 20 | 34 | 34 | 20 | 20 | 20 | 20 | 35 |
| Line width | 135.8 | 127.0 | 141.8 | 160.4 | 119.6 | 0 | 104.2 | 113.3 | 131.5 |

TABLE 6

|  | Example 5 | Example 6 | Comparative example 6 | Comparative example 7 |
|---|---|---|---|---|
| Break point/s | 32 | 25 | 30 | 22 |
| Line width | 163.0 | 130.0 | 138.0 | 115.0 |

TABLE 7

|  | Example 7 | Example 8 | Example 9 | Comparative examples | | | |
|---|---|---|---|---|---|---|---|
|  |  |  |  | 1 | 5 | 8 | 9 |
| Break point/s | 34 | 30 | 21 | 20 | 35 | 22 | 20 |
| Line width | 143.2 | 133.6 | 126.0 | 119.6 | 131.5 | 110.2 | 0 |

TABLE 8

|  | Comparative example 10 | Comparative example 11 | Comparative example 12 |
|---|---|---|---|
| Break point/s | 22 | 25 | 24 |
| Line width | 112.0 | 118.0 | 109.0 |

Adhesive Examples

The examples and comparative examples are prepared according to the components described in table 9. After the components are mixed well, they are coated onto a glass slide using a 50 μm wire rod to form a film, which is then cured under a 365 nm light source with a mask. After curing, the film weight is measured. After immersing in acetone at room temperature for 36 h, the film weight is measured again, and the gel conversion rate is calculated.

TABLE 9

|  | Example 10 | Example 11 | Example 13 |
| --- | --- | --- | --- |
| Photomer 6010 | 5 | 5 | 5 |
| HPMA | 4.5 | 4.5 | 4.5 |
| OXE 02 | 0 | 0 | 0.5 |
| Composition preparation example 1 | 0.5 | 0 | 0 |
| Composition preparation example 2 | 0 | 0.5 | 0 |

Test data of the comparative examples and examples in table 9 are shown in Table 10. The data show that the adhesives in embodiments 10 and 11 in which the photocurable composition of the present inventions are used have significantly higher double bond gel conversion rate under lights than that in comparative example 13 in which oxime ester photoinitiator is used alone.

TABLE 10

|  | Example 10 | Example 11 | Comparative example 13 |
| --- | --- | --- | --- |
| Gel conversion rate | 92.5% | 92.7% | 85.2% |

In summary, there is a significant sensitizing effect when the novel diaroyl carbazole compounds provided by the present invention are used together with carbazolyl oxime ester photoinitiators in photoresist compositions or adhesives. The best sensitising effect is shown when the molar ratio of the diaroyl carbazole compound to the carbazolyl oxime ester photoinitiator is 0.1 to 1.4.

The invention claimed is:

1. A diaroyl carbazole compound, wherein said diaroyl carbazole compound is selected from the group consisting of following compounds and any combination thereof:

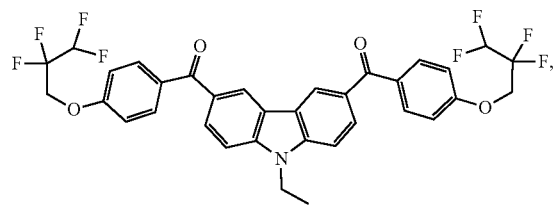

I-1

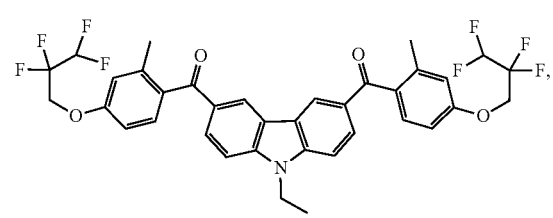

I-2

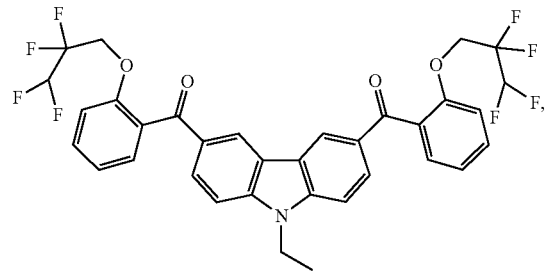

I-3

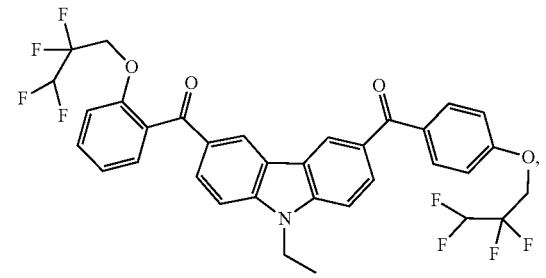

I-4

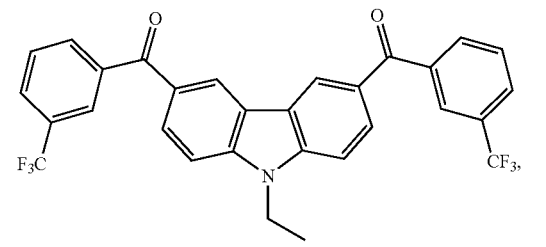

I-5

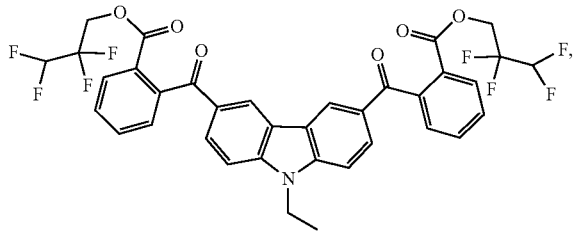

I-6

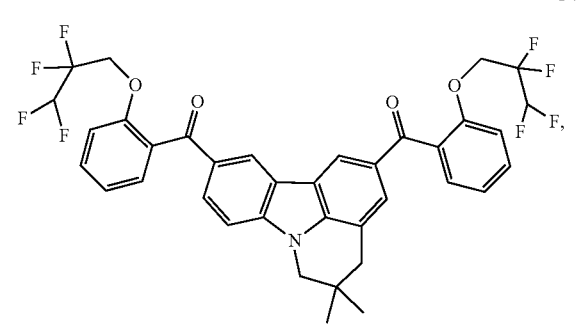

I-7

-continued

II-1
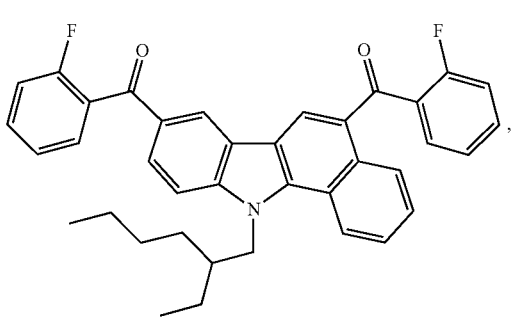

II-2
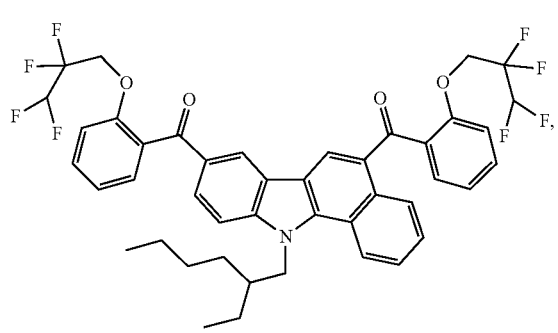

II-3
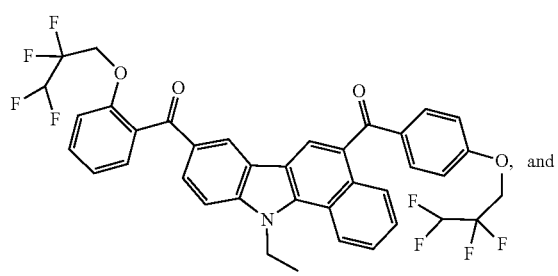

II-4
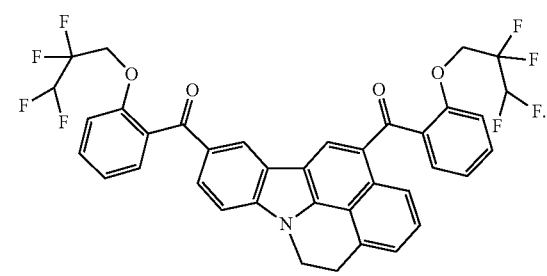

2. A method for preparing the diaroyl carbazole compound of claim 1, comprising preparing a symmetric or asymmetric diaroyl compound via one-step or two-step Friedel-Crafts acylation reaction using a compound of formula III-A or formula III-B as a raw material reacting with corresponding substituted aroyl chloride or acid anhydride; and carrying out an esterification reaction or etherification reaction with an $R_{20}OH$ alcohol compound when any aryl group contains a carboxyl group or a halogen atom, obtaining a diaroyl carbazole compound of formula I-1 to I-7 or formula II-1 to II-4:

III-A
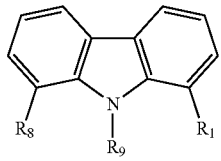

III-B
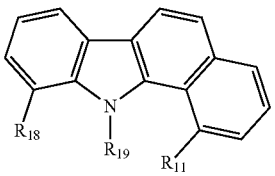

wherein $R_1$, $R_8$, $R_{11}$ and $R_{18}$ are H, $R_9$ is —$CH_2CH_3$, $R_{19}$ is —$CH_2CH_3$ or —$CH_2$—$CH(CH_2CH_3)$—$(CH_2)_3$—$CH_3$, or $R_9$ and $R_1$ optionally form a C6 heterocyclic structure as shown in formula I-7;

or $R_{19}$ and $R_{11}$ optionally form a C6 heterocyclic structure as shown in formula II-4.

3. A photoinitiator composition, comprising at least one diaroyl carbazole compound of claim 1 and at least one carbazolyl oxime ester photoinitiator, wherein the carbazolyl oxime ester photoinitiator comprises at least one oxime ester group

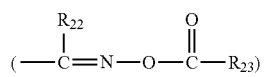

which is connected to a N-substituted carbazole parent structure directly or via a carbonyl group;

wherein, $R_{22}$ is a C1-C12 alkyl unsubstituted or substituted by one or more groups selected from the group consisting of halogen, $OR_{24}$, $SR_{24}$, C3-C8 cycloalkyl, phenyl, C4-C20 heteroaryl, and $COOR_{24}$; or $R_{22}$ is C6-C20 aryl or C4-C20 heteroaryl, each unsubstituted or substituted by one or more groups selected from the group consisting of halogen, C1-C20 alkyl, one or more F-substituted C1-C8 alkyl, CN, $OR_{24}$, $SR_{24}$, and $NR_{25}R_{26}$; or $R_{22}$ is C6-C20 aroyl or C4-C20 heteroaroyl;

$R_{23}$ is selected from the group consisting of C1-C12 alkyl, C6-C20 aryl and C1-C4 alkoxy;

$R_{24}$ is selected from the group consisting of H, C1-C8 alkyl, phenyl, and C1-C20 alkyl phenyl, wherein the C1-C8 alkyl is optionally substituted by one or more of C3-C8 heterocyclic group, F and acetoxy;

$R_{25}$ and $R_{26}$ are each independently C1-C4 alkyl, or $OR_{24}$ substituted C2-C4 alkyl, or $NR_{25}R_{26}$ is a cyclic structure selected from

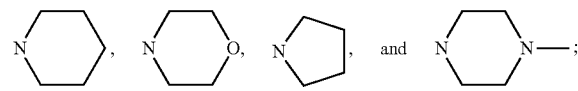

the carbazole parent structure is selected from the group consisting of carbazole, benzocarbazole and dibenzocarbazole, wherein hydrogen atoms on the parent structure are optionally substituted by one or more groups selected from C1-C20 alkyl, halogen, NO$_2$, CN, OR$_{27}$, C6-C20 aroyl, C4-C20 heteroaroyl and 4,5-diphenylimidazole-2-yl in addition to the above oxime ester group or carbonyl group connected with the oxime ester group, and adjacent substituents on the parent structure optionally form a new five-membered to seven-membered ring structure; wherein the C1-C20 alkyl is unsubstituted or substituted by one or more groups selected from halogen, C3-C8 cycloalkyl, C3-C8 heterocyclic group, phenyl, COOR$_{27}$, OR$_{27}$, PO(OC$_n$H$_{2n+1}$)$_2$, and Si(C$_n$H$_{2n+1}$)$_3$, wherein n is an integer from 1 to 4, or the C1-C20 alkyl is interrupted by one or more oxygen atoms when the number of carbon atoms is greater than 3;

R$_{27}$ is C1-C8 alkyl, or C3-C8 heterocyclic alkyl substituted C1-C8 alkyl; wherein aryl or heteroaryl in the C6-C20 aroyl and the C4-C20 heteroaroyl is unsubstituted or substituted by one or more groups selected from halogen, CN,

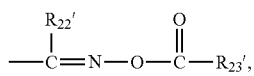

R$_{24}$', OR$_{24}$', SR$_{24}$', NR$_{25}$'R$_{26}$', COOR$_{24}$' and R$_{24}$'SO$_2$; and wherein R$_{22}$', R$_{23}$', R$_{24}$' and NR$_{25}$'R$_{26}$' have the same definition as corresponding R$_{22}$, R$_{23}$, R$_{24}$ and NR$_{25}$R$_{26}$.

4. The photoinitiator composition of claim 3, wherein, the carbazolyl oxime ester photoinitiator is selected from the group consisting of the following compounds and any combination thereof:

IV-1
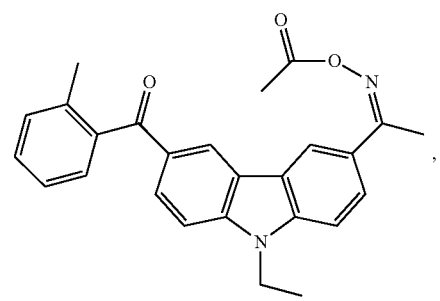

IV-2
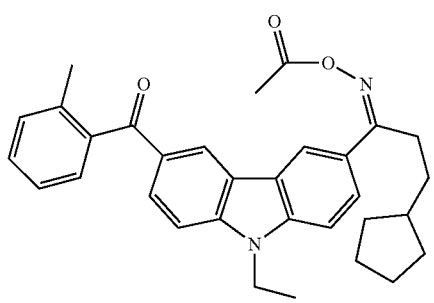

IV-3
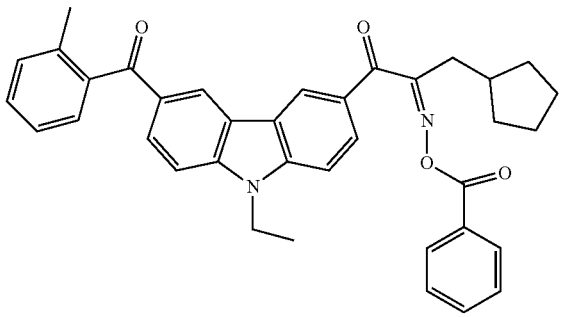

IV-4
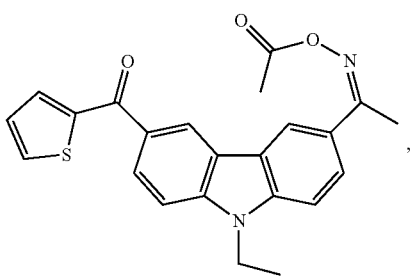

IV-5
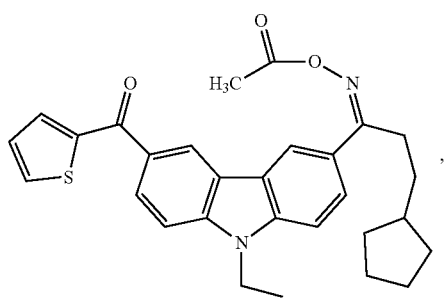

IV-6
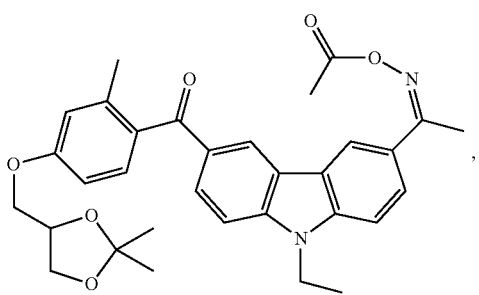

IV-7
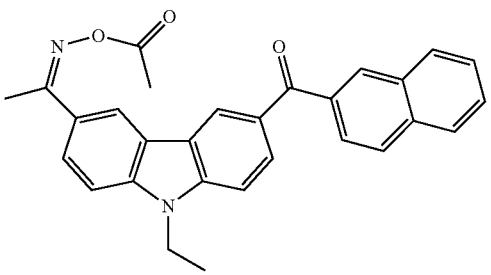

31
-continued
IV-8
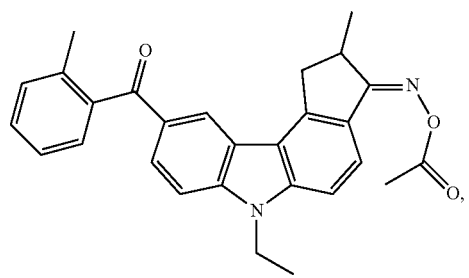
IV-9
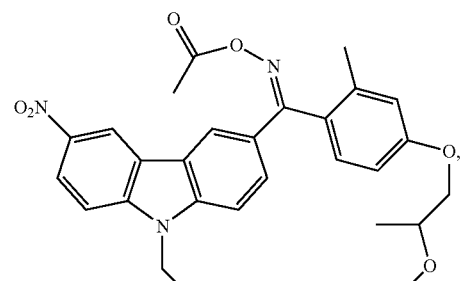
IV-10
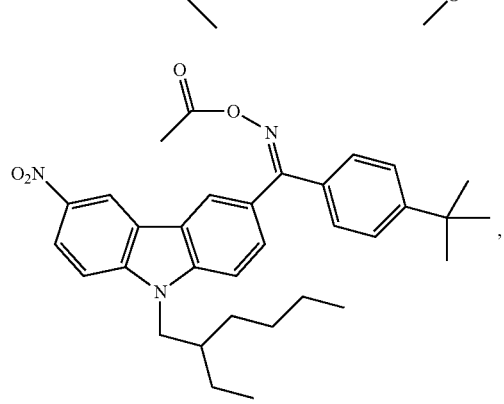
IV-11
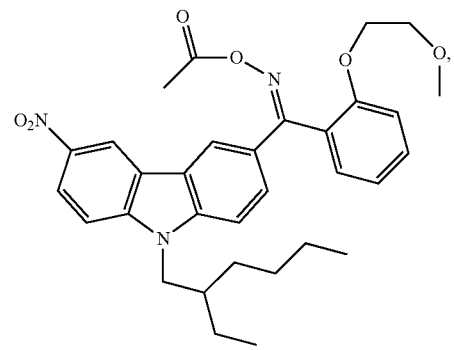
IV-12
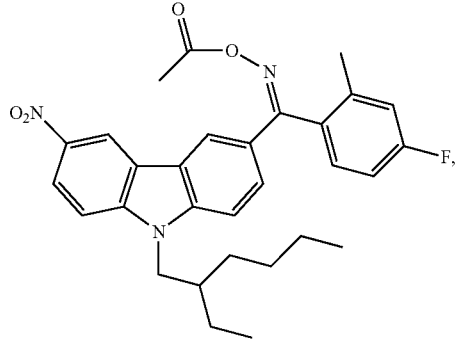
32
-continued
IV-13
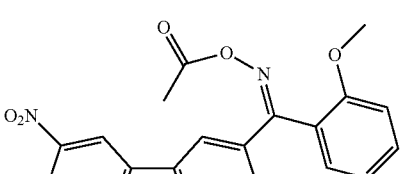
IV-14
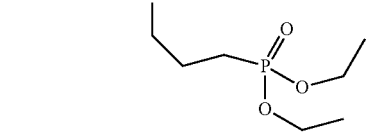
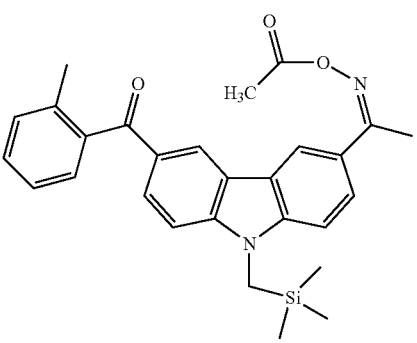
IV-15
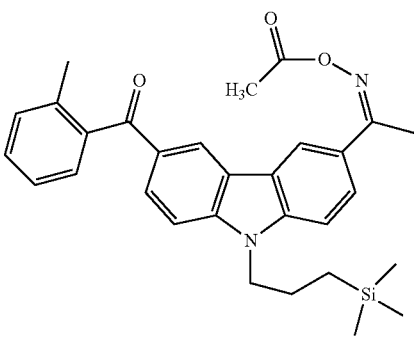
IV-16
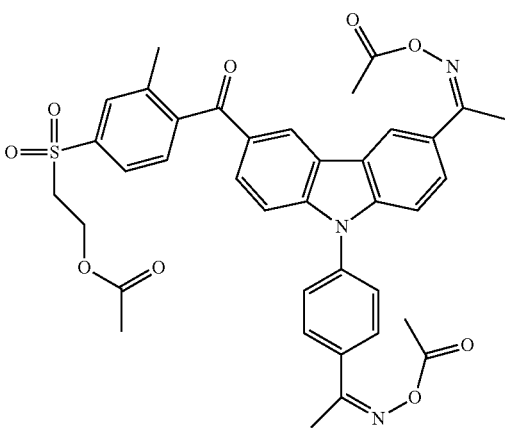

-continued
IV-17
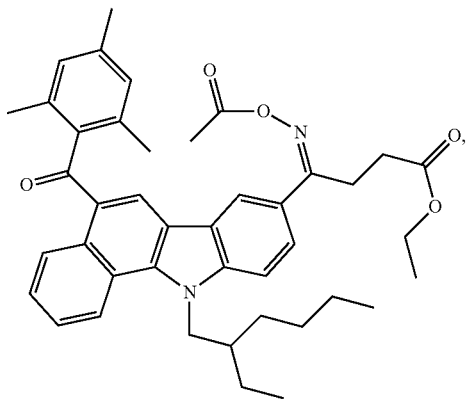
IV-18
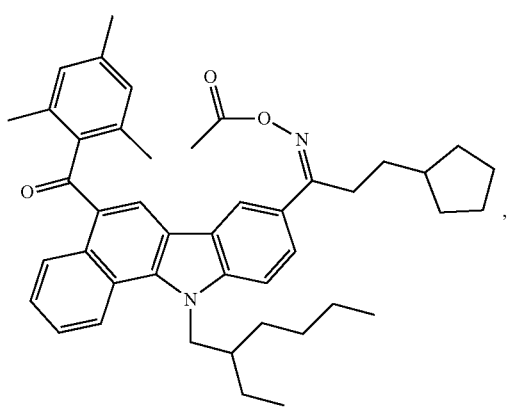
IV-19
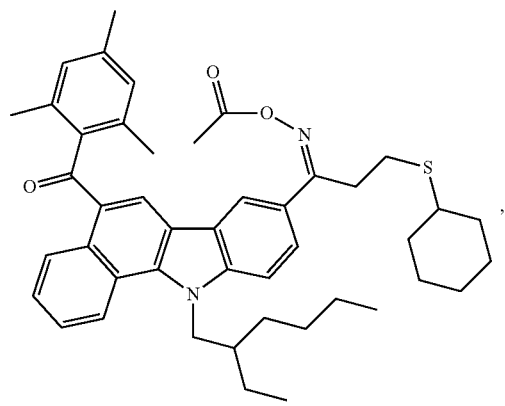
IV-20
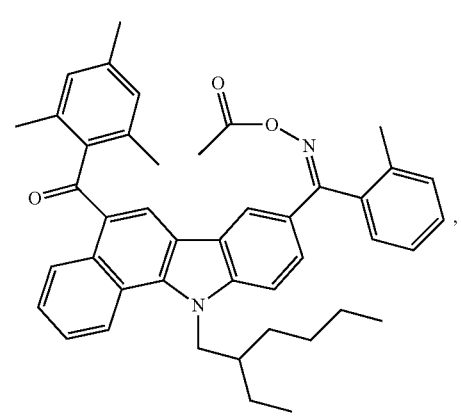
-continued
IV-21
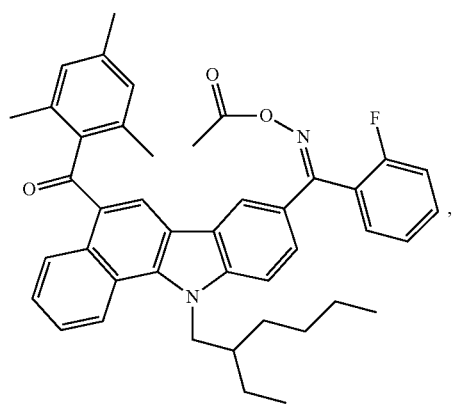
IV-22
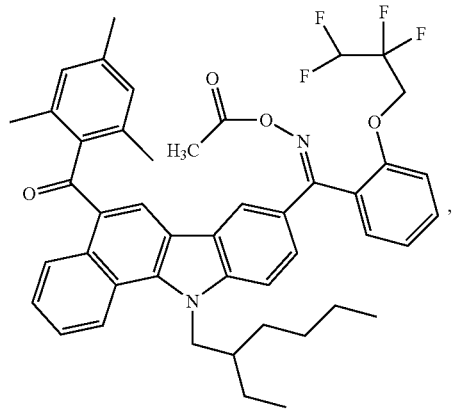
IV-23
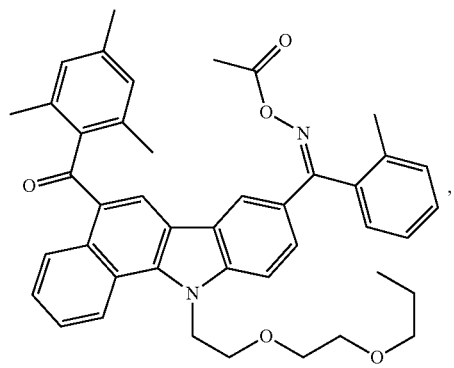
IV-24
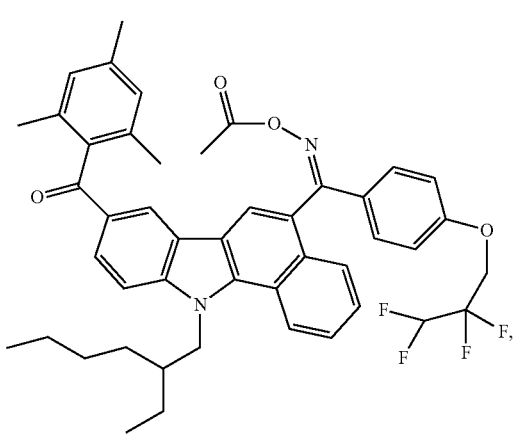

-continued
IV-25
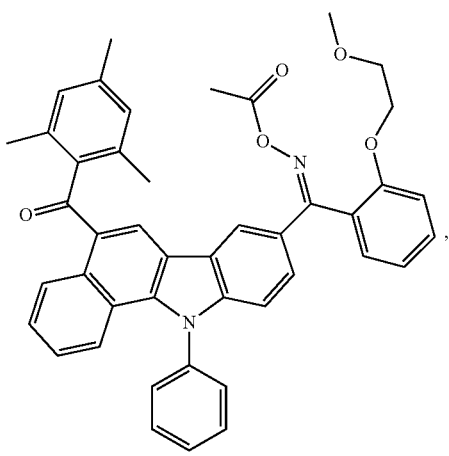
IV-26
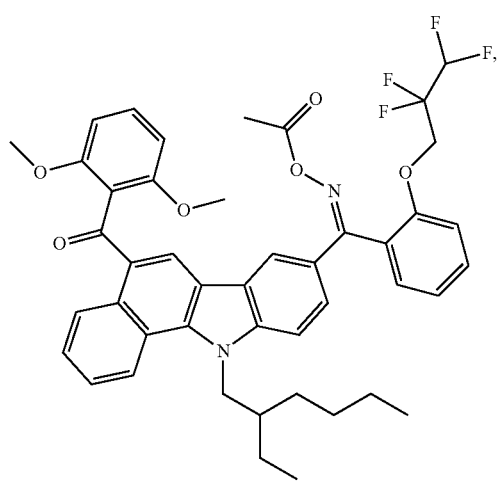
IV-27
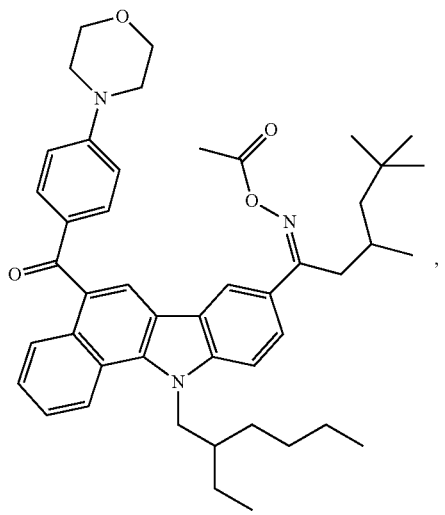
-continued
IV-28
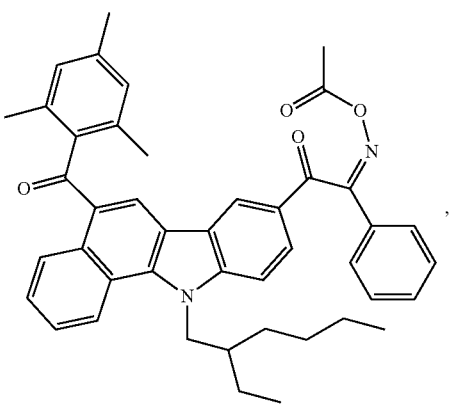
IV-29
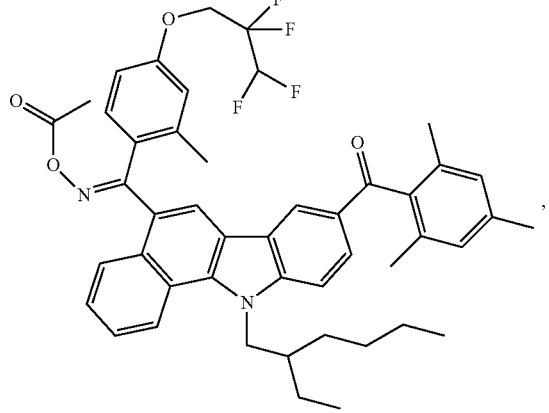
IV-30
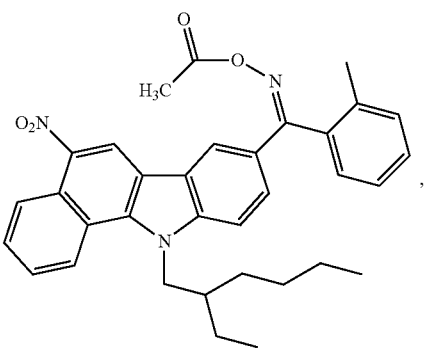
IV-31
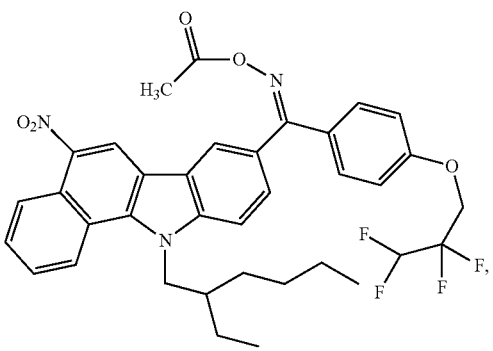

IV-32 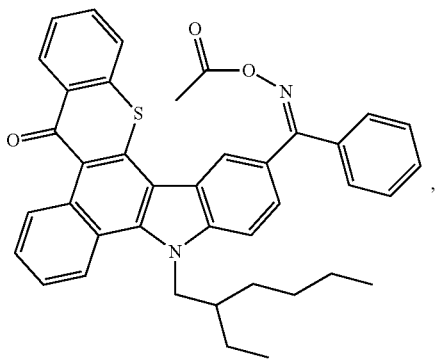

IV-33 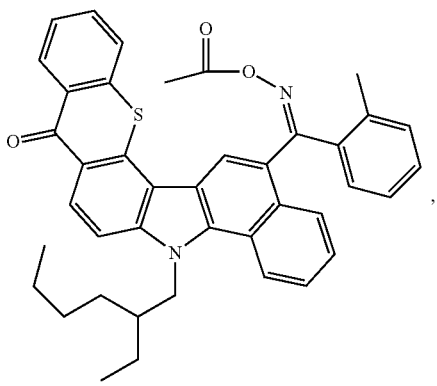

IV-34 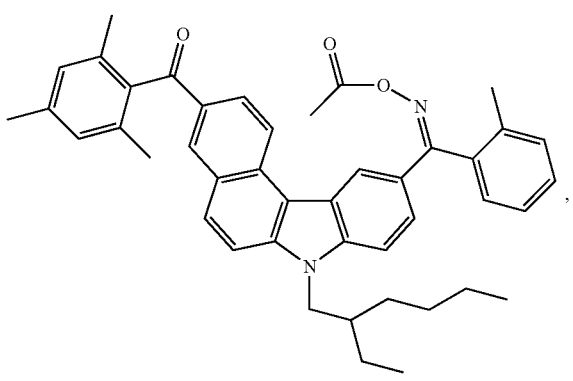

IV-35 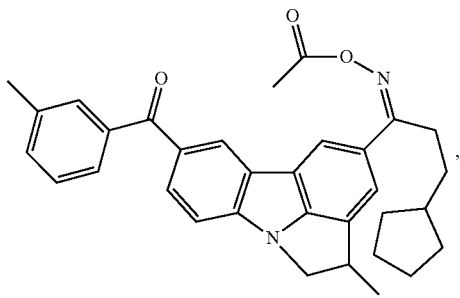

IV-36 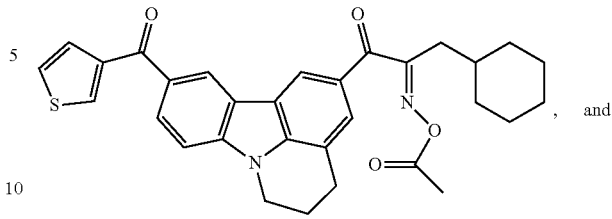, and

IV-37 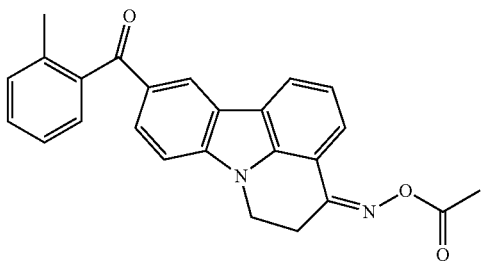.

5. The photoinitiator composition of claim 3, wherein, a molar ratio of the diaroyl carbazole compound to the carbazolyl oxime ester photoinitiator is 0.1:1 to 1.4:1.

6. The photoinitiator composition of claim 5, wherein, a molar ratio of the diaroyl carbazole compound to the carbazolyl oxime ester photoinitiator is 0.22:1 to 1.16:1.

7. A photocurable composition, comprising:
   a. at least one photoinitiator composition of claim 3, and
   b. at least one radically polymerizable compound.

8. The photocurable composition of claim 7, wherein, the radically polymerizable compound is selected from the group consisting of an acrylate compound, a methacrylate compound, a resin containing acrylate or methacrylate groups, and any combination thereof.

9. The photocurable composition of claim 7, wherein, component a accounts for 1-10% by weight of a total weight of all solids.

10. An ink comprising the photocurable composition of claim 7.

11. A coating comprising the photocurable composition of claim 7.

12. An adhesive comprising the photocurable composition of claim 7.

13. A photoresist, comprising:
   a. at least one photoinitiator composition of claim 3,
   b. a multifunctional acrylate monomer,
   c. an alkali soluble resin,
   d. a pigment, and
   e. a solvent.

14. A black photoresist, the photoresist of claim 13, wherein the pigment is well-dispersed carbon black or titanium black.

15. A black matrix prepared from the black photoresist of claim 14.

16. An optical spacer prepared from the black photoresist of claim 14.

17. A color filter device prepared by a filter processing process using the photoresist of claim 13 as a raw material.

* * * * *